(12) United States Patent
Adriaansen

(10) Patent No.: US 10,272,032 B2
(45) Date of Patent: *Apr. 30, 2019

(54) ADENOVIRUS FORUMATIONS

(71) Applicant: Janssen Vaccines & Prevention B.V., Leiden (NL)

(72) Inventor: Janik Adriaansen, Den Haag (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,709

(22) Filed: Apr. 24, 2018

(65) Prior Publication Data

US 2018/0235871 A1  Aug. 23, 2018

Related U.S. Application Data

(63) Continuation of application No. 14/916,539, filed as application No. PCT/EP2014/069654 on Sep. 16, 2014, now Pat. No. 9,974,737.

(30) Foreign Application Priority Data

Sep. 19, 2013 (EP) .................................. 13185200

(51) Int. Cl.
```
A61K 35/761    (2015.01)
C12N 15/86     (2006.01)
C12N 15/861    (2006.01)
C12N 9/00      (2006.01)
A61K 9/00      (2006.01)
C12N 7/00      (2006.01)
A61K 47/02     (2006.01)
A61K 47/10     (2017.01)
A61K 47/12     (2006.01)
A61K 47/18     (2017.01)
A61K 47/26     (2006.01)
A61K 9/08      (2006.01)
A61K 47/40     (2006.01)
A61K 39/00     (2006.01)
```
(52) U.S. Cl.
CPC .............. *A61K 9/0019* (2013.01); *A61K 9/08* (2013.01); *A61K 35/761* (2013.01); *A61K 47/02* (2013.01); *A61K 47/10* (2013.01); *A61K 47/12* (2013.01); *A61K 47/183* (2013.01); *A61K 47/26* (2013.01); *A61K 47/40* (2013.01); *C12N 7/00* (2013.01); *A61K 2039/5256* (2013.01); *A61K 2039/53* (2013.01); *C12N 2710/10034* (2013.01); *C12N 2710/10043* (2013.01); *C12N 2710/10311* (2013.01)

(58) Field of Classification Search
None
See application file for complete search history.

(56) References Cited

U.S. PATENT DOCUMENTS

| | | |
|---|---|---|
| 5,559,099 A | 9/1996 | Wickham et al. |
| 5,837,511 A | 11/1998 | Falck-Pedersen et al. |
| 5,846,782 A | 12/1998 | Wickham et al. |
| 5,851,806 A | 12/1998 | Kovesdi et al. |
| 5,965,541 A | 10/1999 | Wickham et al. |
| 5,981,225 A | 11/1999 | Kochanek et al. |
| 5,994,106 A | 11/1999 | Kovesdi et al. |
| 5,994,128 A | 11/1999 | Fallaux et al. |
| 6,020,191 A | 2/2000 | Scaria et al. |
| 6,040,174 A | 3/2000 | Imler et al. |
| 6,113,913 A | 9/2000 | Brough et al. |
| 6,492,169 B1 | 12/2002 | Vogels et al. |
| 9,115,374 B2 | 8/2015 | Ihnat et al. |
| 9,974,737 B2 * | 5/2018 | Adriaansen .......... A61K 9/0019 |
| 2002/0019041 A1 * | 2/2002 | Kovesdi ............... A61K 47/183 435/235.1 |
| 2002/0031527 A1 | 3/2002 | Wu et al. |
| 2005/0085427 A1 | 4/2005 | Connor et al. |
| 2005/0186225 A1 | 8/2005 | Evans et al. |
| 2008/0234221 A1 | 9/2008 | Connor et al. |

FOREIGN PATENT DOCUMENTS

| | | |
|---|---|---|
| CN | 104027815 A | 9/2014 |
| WO | 199626281 A1 | 8/1996 |
| WO | 200003029 A2 | 1/2000 |
| WO | 2000/29024 A1 | 5/2000 |
| WO | 2003/104467 A1 | 12/2003 |
| WO | 2004055187 A1 | 7/2004 |
| WO | 2006053871 A2 | 5/2006 |
| WO | 2011098837 A1 | 8/2011 |
| WO | 2012110971 A2 | 8/2012 |
| WO | 2015040002 A1 | 3/2015 |

(Continued)

OTHER PUBLICATIONS

Renteria et al., "Development of a Nasal Adenovirus-based Vaccine: Effect of Concentration and Formulation on Adenovirus Stability and Infectious Titer During Actuation from Two Delivery Devices", Vaccine, vol. 38, pp. 2137-2148 (2010).

Radosevic et al., "The Th1 Immune Response to Plasmodium Falciparum Circumsporozoite Protein I s Boosted by Adenovirus Vectors 35 and 26 with a Homologous Insert", Clincal and Vaccine, vol. 17, No. 11, pp. 1687-1694 (Nov. 2010).

Int'l Search Report dated Jan. 13, 2017 in Int'l Application No. PCT/EP2016/073838.

Written Opinion dated Jan. 13, 2017 in Int'l Application No. PCT/EP2016/073838.

(Continued)

*Primary Examiner* — Robert T. Crow
*Assistant Examiner* — John P Nguyen
(74) *Attorney, Agent, or Firm* — Panitch Schwarze Belisario & Nadel LLP

(57) ABSTRACT

This disclosure provides pharmaceutical adenovirus formulations, in particular, liquid pharmaceutical formulations comprising adenoviruses.

20 Claims, 11 Drawing Sheets

(56) References Cited

FOREIGN PATENT DOCUMENTS

WO    2017060329 A1    4/2017

OTHER PUBLICATIONS

Zahn et al., "Ad35 and Ad26 Vaccine Vectors Induce Potent and Cross-Reactive Antibody and T-Cell Responses to Multiple Filovirus Species", PLOS One, vol. 7, No. 12, 13pgs (Dec. 2012).
Loftsson et al., "Pharmaceutical Applications of Cyclodextrins Basic Science and Product Development", Journ. of Pharm., vol. 62, pp. 1607-1621 (2010).
Horwitz, "Adenoviruses", Fields Virology, Third Edition, Chapter 68, in Virology, B.N. Fields et al., eds., 3d ed., Raven Press, Ltd., New York, 23pgs (1996).
Dusautois et al., "Hydroxypropyl Betacyclodextrin: An Enabling Technology for Challenging Pharmaceutical Formulations", Roquette (2009).
Shenk, "Adenoviridae and Their Replication", Adenoviruses, Chapter 67 in Virology, B.N. Fields et al., eds., 3d ed., Raven Press, Ltd., New York, pp. 2111-2148 (1996).
Int'l Search Report dated Nov. 5, 2014 in Int'l Application No. PCT/EP2014/069654.
Written Opinion dated Nov. 5, 2014 in Int'l Application No. PCT/EP2014/069654.
Evans et al., "Development of Stable Liquid Formulations for Adenovirus-Based Vaccines", Journal of Pharmaceutical Sciences, vol. 93, pp. 2458-2476, 2004.
Alteras et al., Production and Formulation of Adenovirus Vectors, Adv. Biochem Engin/Biotechnol, 99, pp. 193-260, 2005.
Int'l Preliminary Report on Patentability dated Nov. 5, 2014 in Int'l Application No. PCT/EP2014/069654.

* cited by examiner

ADENOVIRUS FORMUATIONS

CROSS-REFERENCE TO RELATED APPLICATIONS

This application is a continuation of U.S. patent application Ser. No. 14/916,539, filed Mar. 3, 2016, which is a national phase entry under 35 U.S.C. § 371 of International Patent Application PCT/EP2014/069654, filed Sep. 16, 2014, designating the United States of America and published in English as International Patent Publication WO 2015/040002 A1 on Mar. 26, 2015, which claims the benefit under Article 8 of the Patent Cooperation Treaty to European Patent Application Serial No. 13185200.6, filed Sep. 19, 2013.

TECHNICAL FIELD

This disclosure relates to adenovirus formulations and related pharmaceutical products for use in, e.g., gene therapy and/or vaccine applications. In particular, liquid formulations for adenoviruses are disclosed herein, which improve adenoviral stability by preserving quantity, potency (infectivity) and quality of the contained adenovirus when stored at a temperature between 2° C.-8° C. or higher, while also being compatible with parenteral administration.

BACKGROUND

Adenovirus vectors are considered the most efficient and widely used vehicles for gene delivery. An ongoing challenge in the field of gene therapy and vaccine research is to generate liquid adenovirus formulations that are able to stabilize these viruses for longer periods of time within a realistic storage temperature range for pharmaceutical products, such as from about 2° C. to about 8° C.

Biological activity of an adenovirus depends upon the conformational integrity of at least a core sequence of nucleotides surrounded by an icosahedral capsid structure consisting of the capsid proteins. Unlike traditional organic and inorganic drugs, these are highly complex biological structures and minor chemical or physical stressors can contribute to the degradation of the adenoviral particle. A good formulation of adenovirus preparations is, therefore, of crucial importance to ensure a reasonable shelf-life, but stabilizing these vectors poses particular challenges. Adenoviruses may lose potency as a result of physical instabilities, including denaturation, aggregation (both soluble and insoluble aggregate formation), precipitation and adsorption, as well as chemical instabilities, including hydrolysis, deamidation, and oxidation. Any of these degradation routes can lead to lowered biological activity, and can also potentially result in the formation of by-products or derivatives having increased toxicity and/or altered immunogenicity.

Therefore, a tailored approach is needed to find a robust formulation for adenoviruses ensuring stability over a wide range of conditions. Buffer type, pH and specialized excipients will need to be meticulously optimized to keep an adenovirus chemically, physically and biologically stable. In view of all the factors that can be varied, finding optimal conditions for formulating adenoviruses is burdened with challenges, and the composition of a good formulation is a priori unpredictable.

Lyophilized formulations exist and are stable. However, they tend to be relatively expensive, require time-consuming handling before administration, and potency might, to a certain extent, be lost in the lyophilization process. Liquid formulations that are stable under frozen conditions (−80° C.) exist, but these require specialized shipment and expensive storage facilities, making a reliable cold chain almost impossible, especially at the periphery of the distribution network. A preferred formulation for adenoviruses is, therefore, a liquid formulation that offers adenoviral stability at a temperature range between 2° C. and 8° C., or higher. Such a formulation can be stored in a regular refrigerator and can be administered quickly and easily.

Liquid formulations for adenoviruses have been described previously, for instance, in Evans et al. 2004. The exemplified best formulations in the application are Tris-buffered formulations having a pH ranging between 7.5 and 8.5. It was found herein that the formulations are suboptimal for adenoviruses. Formulations for adenoviruses are also disclosed in WO 00/29024, which mainly relates to lyophilizing techniques. Other formulations for adenoviruses comprising a polyol are mentioned in WO 00/29024.

Accordingly, there is a need in the art to find formulations that improve the adenoviral stability by preserving quantity and potency of the contained adenovirus during storage over a prolonged period of time. The adenoviral stability should also be retained in the case of agitation stress during transport or shear forces during production or clinical use, and under wide-ranging climatic conditions, in particular, at elevated temperature or after repeated freeze/thaw cycles. Furthermore, the formulation should be suitable for the intended route of administration, should be well tolerated and should preferably have a composition with as little components as possible.

BRIEF SUMMARY

Described herein are formulations for adenoviruses that improve the adenoviral-stability by preserving quantity and potency (infectivity) and quality of the adenovirus as compared to previously disclosed formulations. Remarkably, the combination of a citrate buffer having a pH ranging between 5.5 and 6.5, together with hydroxypropyl-beta-cyclodextrin (HBCD), resulted in an outstanding formulation for the preservation of quantity, potency (infectivity) and quality of adenoviruses, therewith improving overall adenoviral-stability as compared to other formulations known in the art.

As with all excipients used for formulation development, some of the components present in the formulation according to this disclosure are separately cited in the prior art. However, it is the very specific combination of several components that gives the present formulation its outstanding properties and stabilizing potential. The exact formulation according to this disclosure was not disclosed in the prior art. In addition, it could not have been foreseen, based on the prior art in this inherently unpredictable field, that the formulation would provide such improved stability to adenoviruses.

This disclosure, therefore, relates to stabilized adenovirus formulations and related pharmaceutical products that can, e.g., be used in gene therapy and/or vaccine applications.

The formulations according to this disclosure comprise a citrate buffer at a pH ranging between 5.5 and 6.5, and further comprise hydroxypropyl-beta-cyclodextrin (HBCD). The formulations additionally comprise a salt and a non-ionic detergent. Optionally, the formulations according to this disclosure, further comprise a 2- or 4-carbon alcohol. The adenoviral formulations of this disclosure are amenable to prolonged storage at 2° C. to 8° C. or ≤−65° C., for more than 6 months, 1 year, 1.5 years, 2 years, or more.

The adenovirus formulations of this disclosure comprise a) a recombinant adenovirus in a b) citrate-buffered solution, which further comprises c) hydroxypropyl-beta-cyclodextrin (HBCD); d) a salt; and e) a non-ionic detergent. In order to preserve the stability of the adenovirus, it is essential that the pH of this formulation ranges between 5.5 and 6.5.

Preferably, the formulation according to this disclosure comprises adenovirus at a titer ranging between about $1 \times 10^7$ vp/mL and $1 \times 10^{13}$ vp/mL.

In a preferred embodiment according to this disclosure, the citrate concentration in the formulation ranges between about 5 mM and 30 mM.

Hydroxypropyl-beta-cyclodextrin (HBCD) is the preferred cryoprotectant. HBCD is preferably present in a concentration ranging between about 1% (w/w) and 10% (w/w).

Sodium chloride (NaCl) is the preferred salt, which is preferably present at a concentration ranging between about 20 mM and 200 mM.

Polysorbate-80 is the preferred non-ionic detergent that preferably has a concentration ranging between about 0.005% (w/w) and 0.5% (w/w).

In a more preferred embodiment according to this disclosure, the formulation has a pH ranging between about 5.7 and 6.3, and comprises citrate at a concentration ranging between about 5 mM and 30 mM; HBCD at a concentration ranging between 1% (w/w) and 10% (w/w); NaCl at a concentration ranging between 20 mM and 200 mM; and Polysorbate-80 at a concentration ranging between about 0.01% (w/w) and 0.05% (w/w).

In another preferred embodiment according to this disclosure, the formulation has a pH ranging between about 5.8 and 6.2, and comprises citrate at a concentration ranging between about 15 mM and 25 mM; HBCD at a concentration ranging between 3% (w/w) and 8% (w/w); NaCl at a concentration ranging between 50 mM and 100 mM; and Polysorbate-80 at a concentration ranging between about 0.01% (w/w) and 0.03% (w/w).

In an even more preferred embodiment, the formulation according to the disclosure has a pH of about 6 and comprises citrate at a concentration of about 20 mM; HBCD at a concentration of about 5% (w/w); NaCl at a concentration of about 75 mM; and Polysorbate-80 at a concentration of about 0.02% (w/w).

It was demonstrated herein that the addition of a 2- or 4-carbon alcohol, in particular, ethanol, into the formulation of this disclosure, unexpectedly strongly protected adenoviruses against freeze/thaw damage and consequently worked as a cryoprotectant.

Therefore, in a preferred embodiment, the formulation according to the disclosure further comprises a 2- or 4-carbon alcohol. In an even more preferred embodiment, the formulation according to the disclosure comprises ethanol. The ethanol concentration is preferably ranging between about 0.1% (w/w) and 1% (w/w).

In a preferred embodiment according to this disclosure, the formulation has a pH ranging between about 5.7 and 6.3, and comprises citrate at a concentration ranging between about 5 mM and 30 mM; HBCD at a concentration ranging between 1% (w/w) and 10% (w/w); NaCl at a concentration ranging between 20 mM and 200 mM; Polysorbate-80 at a concentration ranging between about 0.01% (w/w) and 0.05% (w/w); and ethanol at a concentration ranging between about 0.2% (w/w) and 0.6% (w/w).

In another preferred embodiment according to this disclosure, the formulation has a pH ranging between about 5.8 and 6.2, and comprises citrate at a concentration ranging between about 15 mM and 25 mM; HBCD at a concentration ranging between 3% (w/w) and 8% (w/w); NaCl at a concentration ranging between 50 mM and 100 mM; Polysorbate-80 at a concentration ranging between about 0.01% (w/w) and 0.03% (w/w); and ethanol at a concentration ranging between about 0.2% (w/w) and 0.6% (w/w).

In an even more preferred embodiment, the formulation according to the disclosure has a pH of about 6 and comprises citrate at a concentration of about 20 mM; HBCD at a concentration of about 5% (w/w); NaCl at a concentration of about 75 mM, Polysorbate-80 at a concentration of about 0.02% (w/w); and ethanol at a concentration of about 0.4% (w/w).

In another preferred embodiment, the formulation according to the disclosure has a pH of about 6 and comprises citrate at a concentration of about 20 mM; HBCD at a concentration of about 5% (w/w); NaCl at a concentration of about 80 mM, Polysorbate-80 at a concentration of about 0.025% (w/w); and ethanol at a concentration of about 0.4% (w/w).

In an even more preferred embodiment, the formulation according to the disclosure has a pH of about 6 and comprises citrate at a concentration of about 20 mM; HBCD at a concentration of about 5% (w/w); NaCl at a concentration of about 80 mM; Polysorbate-80 at a concentration of about 0.025% (w/w); and ethanol at a concentration of about 0.4% (w/w).

In another preferred embodiment of this disclosure, the formulations are (frozen) liquid formulations. In yet another embodiment, the formulations of this disclosure are suitable for parenteral use.

In one embodiment, the formulations according to this disclosure are contained in a vial. In another embodiment, the formulations are contained in a bag or a bottle. In yet another embodiment, the formulations are contained in a syringe or cartridge.

This disclosure also relates to a method of preserving an adenovirus that comprises preparing a formulation according to this disclosure.

In yet another embodiment, this disclosure relates to a method of preserving an adenovirus that comprises preparing a formulation as described herein and storing the formulation at a temperature ranging between 2° C. and 8° C.

The enhanced long-term stability over a wide temperature range results in an extended shelf-life of the virus formulations disclosed herein, allowing for storage and eventual host administration of these formulations over preferably about a 1- to 2-year period, or more, with acceptable losses in virus potency (i.e., not more than 0.3 log per two years between 2° C. and 8° C.). In addition, formulations of this disclosure show stability during exposure to elevated temperatures, extended freeze/thaw cycles and agitation.

DETAILED DESCRIPTION

Figure 1:
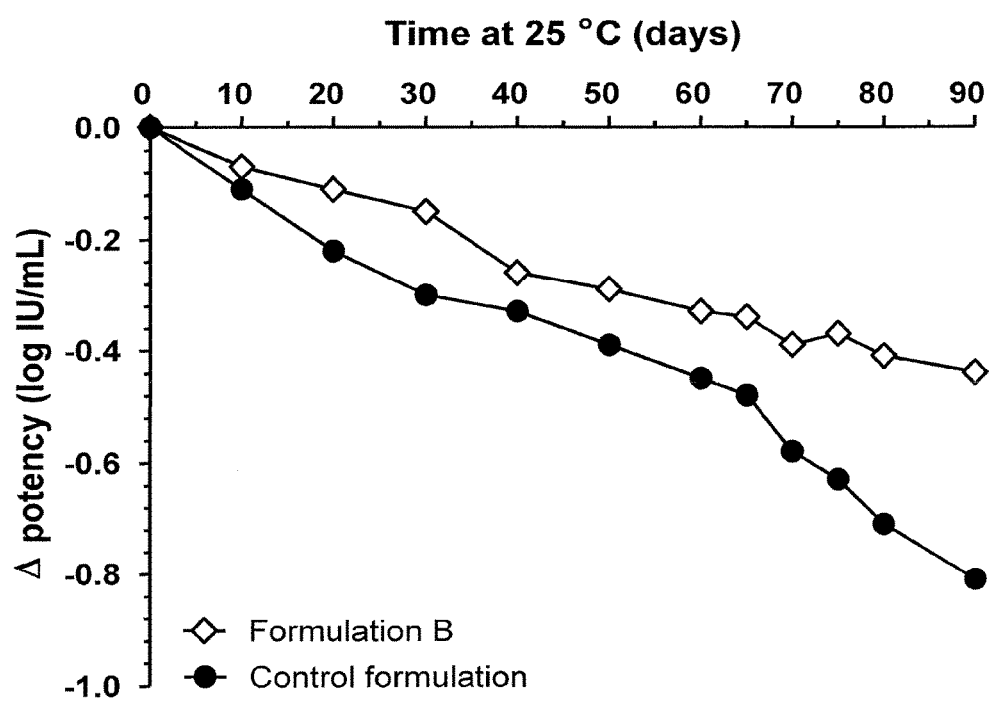
FIG. 1: Potency (in log IU/mL) loss (Δ) of Ad26 during accelerated temperature at 25° C. in Formulation B (open diamonds) and control formulation (closed circles). Mean Δ potency (n=4) is shown, reflecting potency$_{stressed\ sample}$−potency$_{control\ sample}$. Potency has been measured by QPA.

As mentioned previously, there is a need in the art to find formulations that improve the adenoviral stability by preserving quantity and potency of the contained adenovirus during storage over a prolonged period of time.

Several references disclose the use of specific components for the formulation of adenoviruses. Altaras et al. discloses citrate as part of a large list of possible inhibitors of free-radical oxidation. The list also contains the combination of EDTA and ethanol (EDTA/ethanol), which is identified as a further inhibitor of free-radical oxidation. The formulation of this disclosure uses citrate as a buffer and not as an anti-oxidant.

Renteria et al. identifies hydroxypropyl-beta-cyclodextrin (HBCD) as one of the additives used to promote the stability of certain proteins and to avoid aggregation during nasal administration. Renteria et al. discloses the use of hydroxypropyl-beta-cyclodextrin in the context of a formulation appropriate for nasal administration enhancing mucosal uptake. All proteins are very different compared to live viruses such as adenoviruses, in terms of structure, charge, and size. Consequently, the stabilizing mechanism for adenoviruses is completely different and unpredictable in view of the stabilizing mechanism for proteins.

WO 029024 discloses hydroxypropyl-beta-cyclodextrin as part of a large list of possible lyoprotectants used for preparing a freeze-dried formulation. WO 029024 relates to a freeze-dried composition as opposed to a liquid composition as disclosed in this disclosure. The advantage of a liquid formulation is that it is less expensive, and the handling before administration is less time consuming and less prone to clinical dosing or reconstitution mistakes. Furthermore, scale-up of lyophilization processes can be a cumbersome endeavor.

Described herein are formulations for adenoviruses that improve the adenoviral stability by preserving quantity and potency (infectivity) and quality of the adenovirus as compared to previously disclosed formulations.

The formulations of the disclosure comprise at least one recombinant adenovirus. The construction of adenoviral vectors is well understood in the art and involves the use of standard molecular biological techniques, such as those described in, for example, Sambrook et al., *Molecular Cloning, a Laboratory Manual,* 2d ed., Cold Spring Harbor Press, Cold Spring Harbor, N.Y. (1989); Watson et al., *Recombinant DNA,* 2d ed., Scientific American Books (1992); and Ausubel et al., *Current Protocols in Molecular Biology,* Wiley Interscience Publishers, NY (1995), and other references mentioned herein. In short, the adenoviral vector can be deficient in at least one essential gene function of the E1 region, e.g., the E1a region and/or the E1b region, of the adenoviral genome that is required for viral replication. As known to the skilled person for producing adenovirus, in case of deletions of essential regions from the adenovirus genome, the functions encoded by these regions have to be provided in trans, preferably by the producer cell, for instance, integrated in the genome, or in the form of so-called helper adenovirus or helper plasmids, when producing the recombinant adenovirus.

Propagation of a recombinant adenovirus has been described in detail in: U.S. Pat. No. 6,492,169 or in WO 03/104467, U.S. Pat. Nos. 5,559,099, 5,837,511, 5,846,782, 5,851,806, 5,994,106, 5,994,128, 5,965,541, 5,981,225, 6,040,174, 6,020,191, and 6,113,913, and Thomas Shenk, "Adenoviridae and their Replication," M. S. Horwitz, "Adenoviruses," Chapters 67 and 68, respectively, in *Virology,* B. N. Fields et al., eds., 3d ed., Raven Press, Ltd., New York (1996), each of which is incorporated herein by this reference. The replication-deficient adenoviral vector can be generated by using any species, strain, subtype, or mixture of species, strains, or subtypes, of an adenovirus or a chimeric adenovirus as the source of vector DNA (see, for instance, WO 96/26281, WO 00/03029). In certain embodiments of this disclosure, serotypes of human adenovirus include any one of serotypes 2, 4, 5, 7, 11, 26, 34, 35, 36, 48, 49 or 50 or any hybrid or mutated adenovirus serotypes. In a preferred embodiment of this disclosure, the recombinant adenovirus is from human adenovirus serotype 5, 26 or 35.

In further embodiments, the adenovirus of the disclosure is a simian adenovirus, preferably a chimpanzee or gorilla adenovirus. These adenoviruses generally have a low seroprevalence and/or low pre-existing neutralizing antibody titers in the human population.

In further embodiments, the adenovirus of the disclosure further comprises heterologous nucleic acid. Suitable heterologous nucleic acid is well known to the skilled person and, for instance, may include transgene open reading frames, for instance, open reading frames coding for polypeptides against which an immune response is desired when the vector is used for vaccination purposes, e.g., transgenes suitable to generate an immune response against malaria (see, e.g., WO 2004/055187), HIV, tuberculosis (see, e.g., WO 2006/053871), certain viruses, etc., all well known to the skilled person. In fact, the nature of the transgene is not critical to the current disclosure, it may be any heterologous nucleic acid sequence, and, hence, needs no further elaboration here.

The term "stability" as used herein refers to the relative resistance to degradation of adenovirus particles in a formulation retaining its potency on the timescale of its expected usefulness. Preferably, the potency shows a decrease of not more than 0.3 log per two years at 2° C. to 8° C.

The term "potency" as used herein refers to a measure of adenovirus activity expressed in terms of infectious units measured in a cell-based potency assay, which is described hereunder.

A composition according to the disclosure shows a decrease in potency of not more than 0.4 log per 60 days and a decrease in titer of not more than 0.3 log per 60 days in an accelerated stability study, which study is performed by incubation of the formulations at 25° C.±2° C. during a 1- to 3-month period.

A composition according to the disclosure also shows a decrease in potency of not more than 0.2 log per ten cycles in a study wherein vials are subjected to repeated freeze/thawing cycles followed by 24 hours of agitation at room temperature in a horizontal orientation at 200 rpm.

By "pharmaceutically acceptable excipient" is meant any inert substance that is combined with an active molecule such as a virus for preparing an agreeable or convenient dosage form. The "pharmaceutically acceptable excipient" is an excipient that is non-toxic to recipients at the dosages and concentrations employed, and is compatible with other ingredients of the formulation comprising the viral preparation. Examples of excipients are cryoprotectants, non-ionic detergents, buffers, salts and inhibitors of free-radical oxidation.

The term "by-product" includes undesired products, which detract or diminish the proportion of therapeutic/prophylactic adenovirus in a given formulation. Typical by-products include aggregates of the adenovirus and fragments of the adenovirus, resulting from, e.g., protein denaturation, deamidation, hydrolysis or combinations thereof. Typically, aggregates are complexes that have a molecular weight greater than the isolated virus particle.

A formulation that improves the adenoviral stability, also named a "stable formulation" as used herein is a formulation in which the adenovirus therein essentially retains its physical and/or chemical integrity and/or biological activity upon storage. Stability can be assessed by determining different characteristics such as the quantity (of adenovirus in a formulation), the potency, and/or other quality aspects of the adenovirus in the formulation over a period of time and under certain storage conditions. These characteristics of an adenovirus formulation can be measured at elevated temperatures (predictive for real-time temperatures) or under other stress conditions, for instance, formulations can be subjected to incubation at 25° C. or subjected to freeze/thaw cycles and agitation in order to study effects of different formulations maximizing shelf-life. The characteristics that determine the stability may be determined by at least one of the methods selected from the group consisting of visual inspection, virus particle quantitative polymerase chain reaction (vp-QPCR), QPCR-based Potency Assay (QPA), Reverse Phase High Performance Liquid Chromatography (RP-HPLC) and Differential Centrifugal Sedimentation (DCS), Thermal Melting Assay (TMA), Turbidimetry, and Intrinsic Fluorescence.

Virus Particle Quantitative Polymerase Chain Reaction (vp-QPCR)

The vp-QPCR was developed for the quantification of adenovirus particles using primers that target a 100 bp region of the CMV promoter of the transgene cassette present within the adenovirus vector. Briefly, this QPCR method relies on the exonuclease activity of Taq polymerase, which results in degradation of a specific fluorescent probe annealed in the middle of the 100 bp amplicon. The probe is covalently linked to a light emitter and a quencher, and its degradation frees the emitter from the quencher with a consequent fluorescence emission proportional to the amount of template. Quantitative values are obtained from the threshold cycle (Ct), the cycle at which an increase in fluorescence signal exceeds a threshold value. The threshold for detection of DNA-based fluorescence is set slightly above background. The number of cycles at which the fluorescence exceeds the threshold is called the threshold cycle (Ct) or, according to the MIQE guidelines, quantification cycle (Cq) (Bustin et al., 2009). During the exponential amplification phase, the target DNA sequence doubles every cycle. For example, a DNA sample of which the Ct precedes that of another sample by three cycles contained $2^3=8$ times more template. Consequently, a higher Ct value represents a lower amount of target DNA and a lower Ct value represents a high availability of target DNA. Absolute quantification can be performed by comparing a standard curve generated by a serial dilution of a stock adenovirus of which the concentration has been determined by the optical density at 260 nm ($OD_{260}$). The Ct values of the test material are plotted against the Ct values of the standard curve, which generates an accurate and precise number of vector particles.

When used as readout after incubation on E1-competent cells (QPA, see below), more degraded samples will lead to higher delta (t=0 subtracted) Ct values and more stabilizing formulations will lead to lower Ct values.

QPCR-Based Potency Assay (QPA)

To quantify adenovirus potency, the QPA combines QPCR with a tissue culture-based infectivity assay. The assay is based on the experimental observation that the appearance of newly synthesized viral DNA is very rapid after inoculation of a cell-monolayer, and is proportional to the virus input concentration over a large range of multiplicity of infection (MOI). Dilutions of samples (non-endpoint diluted) are inoculated onto HEK293 cell monolayers in a 96-well plate. The infection is allowed to proceed for 3 hours at 35° C. Wells are aspirated and replenished with medium that does not contain adenoviruses. Plates are incubated for an additional 42 hours prior to cell lysis by means of TRITON® X-100 solution and a single freeze/thaw step in order to release adenovirus DNA. A QPCR is performed on diluted cell lysates according to the method described above. The infectivity titer is calculated by comparison to a standard curve generated by the Ct values of a sample of known infectivity, which is determined by end-point titration. Alternatively, the delta potency can be expressed directly as Ct values since the infectivity titer, or potency, is directly correlated to the Ct values. Especially in comparing relative differences in potency between formulations, this is a quick and reliable method.

Reverse Phase High Performance Liquid Chromatography (RP-HPLC)

In order to determine some quality aspects of an adenovirus, one can analyze adenoviral protein profiles by Reverse Phase High Performance Liquid Chromatography (RP-HPLC). HPLC separates components of a mixture by using a variety of chemical interactions between the sample, the mobile phase (a buffer or solvent) and the stationary phase (a chromatographic packing material in a column). A high-pressure pump moves the mobile phase through the column and a detector shows the retention times ($t_R$; time between sample injection and the appearance of the peak maximum) of the molecules using UV absorbance detection at 280 nm. The separation of RP-HPLC is based on differences in hydrophobicity. The non-polar stationary phase is made up of hydrophobic alkyl chains (chain lengths: C4, C8 and C18). The polar mobile phase is water with 0.1% trifluoroacetic (TFA). Compounds that bind to the columns are eluted using an increasing concentration of acetonitrile with 0.1% TFA. In general, an analyte with a larger hydrophobic surface area has a longer retention time, whereas the presence of polar groups reduce retention time. A typical adenoviral RP-HPLC profile consists of 10 or 14 proteins, including core protein (VII), penton base (III) and hexon (II).

Differential Centrifugal Sedimentation (DCS)

DCS is a method to measure particle size distributions (aggregation) by sedimentation. In a disc centrifuge, particles settle in a sucrose gradient (of known viscosity and density) under high gravitational forces according to Stokes' law. Sedimentation velocity increases with the square of the particle diameter, so particles that differ in size by only a few percent settle at significantly different rates. The time needed to reach the detector is used to calculate the size of the particles. The measurement range for this method is about 0.02 to 30 microns.

Thermal Melting Assay (TMA)

The thermal melting assay (TMA) can be used to determine the melting temperature ($T_m$) of adenovirus in experimental formulations, which is the temperature where the viral capsid denatures. This viral disintegration can be measured real-time using a dsDNA intercalating fluorescent dye. This fluorescent dye only gives a fluorescence signal when bound to DNA, which is released when the viral particle disintegrates. The exponential fluorescence increase upon capsid melting can be measured using a common QPCR machine during a stepwise increase in temperature. Samples are diluted to the same concentration (range is $4 \times 10^9$ to $1 \times 10^{12}$ vp/mL) in the specific formulations and mixed with SYBRGreen dye (1× final concentration) in a volume of 50 μL. The temperature was increased 0.5° C. per 30 seconds starting from 30° C. up to 79° C. From the fluorescent raw data, first and second derivatives are calculated and melting temperature is read at the intercept of the second derivative with the x-axis. Higher melting temperatures ($T_m$) may be indicative of a more stabilizing formulation.

Turbidity Assay

Turbidimetry measures the loss of intensity of transmitted light due to scattering of particles in samples (apparent absorbance), detected at a wavelength where the molecules in the sample do not absorb light (e.g., 350 nm for samples in which proteins are the main chromophore). When molecules aggregate or form supramolecular complexes, the light scattering, which was random when coming from the separate particles, now becomes coherent, and thereby the measured intensity increases. This makes light scattering and turbidimetry useful techniques for detecting aggregation and complex formation or dissociation.

In the turbidity assay, samples are transferred in triplicate to a UV-transparent, flat-bottom microplate. The plate is covered with a UV-transparent seal. Absorbance spectra are recorded by a microplate reader between 230 and 500 nm, and the absorbance at 975 nm is measured to determine and possibly correct for differences in optical path length. Control samples consisting of the formulations without the adenovirus are included in the assay to correct for scattering or absorbing matrix components if required. The apparent absorbance at 350 nm is used as a quantitative measure for turbidity.

The turbidity assay is stability-indicating for adenovirus samples. Virus aggregation leads to an increase in turbidity and capsid dissociation to a decrease. The assay precision is <5% (CV %) at turbidity values >1 NTU.

The obtained turbidity for stressed samples should always be compared to the control samples. Since an increase or decrease after applied stress is dependent on the degradation pathway and specific for each Active Pharmaceutical Ingredient (API), it cannot be predicted. A change (higher or lower) compared to the t=0 samples is indicative of a less stable formulation. Stressed samples comparable to the t=0 samples are expected to be more stable.

Intrinsic Fluorescence Assay

The adenoviral capsid proteins contain aromatic amino acids that reemit light after excitation, in particular, tryptophan, and to a lesser extent, tyrosine and phenylalanine. The emission maximum and quantum yield of tryptophan depend strongly on the polarity of its environment. In a polar, aqueous environment (e.g., the surface of a globular protein) the quantum yield is relatively low, while in an apolar environment (e.g., the inside of an aggregate) the quantum yield increases. This feature makes tryptophan fluorescence a useful tool for studying protein conformational change, aggregation, and molecular interactions.

In the intrinsic fluorescence assay, samples are transferred in triplicate to a UV-transparent, flat-bottom microplate. The plate is covered with a UV-transparent seal. Tryptophan fluorescence is measured by a microplate reader using an excitation filter with a center wavelength of 280 nm and a bandwidth of 10 nm, and an emission filter with a center wavelength of 340 nm and a bandwidth of 10 nm. Bottom optic is used to minimize the influence of the seal and the meniscus shape.

The fluorescence intensity is known in the art to be a sensitive measure of adenovirus stability. Either an increase or a decrease may be observed upon stress, depending on the nature of the changes occurring in the sample. Protein unfolding and capsid dissociation is expected to lead to a decrease in intrinsic fluorescence, and aggregation is expected to lead to an increase. The precision of the assay is <5% (CV %) in the range used.

The obtained fluorescence for stressed samples should always be compared to the control samples. Since an increase or decrease after applied stress is dependent on the degradation pathway and specific for each Active Pharmaceutical Ingredient (API), it cannot be predicted. A change (higher or lower) compared to the t=0 samples is indicative of a less stable formulation. Stressed samples remaining close to the t=0 sample values are more stable.

An adenovirus "retains its physical stability" in a pharmaceutical formulation, if it, amongst others, shows minimal loss (i.e., 0.3 log/2 years) in terms of quantity and potency, and displays no major protein modifications. Additionally, no signs of aggregation, precipitation, change of color and/or clarity upon visual examination should be observed.

"About" as used in the present application means±10%, unless stated otherwise.

This disclosure relates to formulations that stabilize an adenovirus and to related pharmaceutical products, preferably for use in gene therapy and/or vaccine applications. A preferred stabilized virus-containing formulation disclosed herein is a liquid adenovirus formulation, which shows improved adenoviral stability when stored in about the 2° C. to 8° C. range while also being compatible with parenteral administration. These formulations can, however, also be stored at lower temperatures, e.g., −20° C. or lower, −40° C. or lower, −65° C. or lower, or −80° C. or lower. They may also be more stable at temperatures above 8° C., e.g., 25° C. or even higher.

These formulations that are able to stabilize an adenovirus comprise a citrate buffer, hydroxypropyl-beta-cyclodextrin (HBCD), a salt and a non-ionic detergent, as well as optional additional components that enhance stability to the added virus. The pH of the buffer lies between 5.5 and 6.5.

The formulations of this disclosure provide stability to adenoviruses at varying virus concentrations, mono- or multivalent, and may be administered to a variety of vertebrate organisms, preferably mammals and especially humans. The stabilized viral formulations of this disclosure are adenoviral-based compositions that can, for instance, be administered as a vaccine that may offer a prophylactic advantage to previously uninfected individuals and/or provide a therapeutic effect.

A preferred aspect of the disclosure is a formulation for recombinant adenoviruses (i.e., an adenovirus containing a whole or a portion of a transgene that is expressed within the target host subsequent to host administration, such as in any mammalian/human gene therapy- or gene vaccination-based methodology available to the skilled artisan) that shows enhanced stability characteristics described herein with a virus concentration in the range from about $1 \times 10^7$ vp/mL (virus particles/mL) to about $1 \times 10^{13}$ vp/mL. A more preferred range is from about $1 \times 10^9$ to $1 \times 10^{13}$ vp/mL, with an especially preferred virus concentration being from about $1 \times 10^{10}$ to $5 \times 10^{12}$ vp/mL. Therapeutic or prophylactic compositions of the formulations of this disclosure can be administered to an individual in amounts sufficient to treat or prevent the respective disorder. The effective amount for human administration may, of course, vary according to a variety of factors such as the individual's condition, weight, sex and age. Other factors include the mode of administration. In a preferred embodiment, the formulations of this disclosure are suitable for parenteral use.

The formulations of this disclosure are citrate-buffered solutions having a pH ranging between 5.5 and 6.5, further comprise hydroxypropyl-beta-cyclodextrin (HBCD) and optionally comprising a 2- or 4-carbon alcohol. Unexpectedly, the combination has proven to be an outstanding formulation for the preservation of quantity, potency (infectivity) and quality of adenoviruses, as demonstrated herein.

In a preferred embodiment, the concentration of citrate is ranging between about 5 mM and 30 mM, e.g., between about 5 mM and 25 mM, e.g., between about 10 mM and 25 mM, e.g., about 20 mM.

Another essential component in these formulations that contributes to virus stabilization over large temperature ranges and for prolonged storage periods is HBCD, which is used as a cryoprotectant. In a preferred embodiment, the concentration of HBCD is ranging between about 1% (w/w) to 10% (w/w), e.g., between about 3% (w/w) to 8% (w/w), e.g., between about 4% (w/w) to 6% (w/w), e.g., about 5% (w/w).

An additional component of the formulations of this disclosure is salt. Salt enhances viral stability. A purpose of inclusion of a salt in the formulation is to attain the desired ionic strength or osmolality and additionally optimize electrostatic interactions. Salt is present at an osmolality that is physiologically acceptable to the host. Contributions to ionic strength may come from ions produced by the buffering compound as well as from the ions of non-buffering salts. Salts that are appropriate for the formulations of this disclosure include, but are not limited to, sodium chloride (NaCl), Calcium chloride ($CaCl_2$) or manganese chloride ($MnCl_2$). In contrast to the prior art, magnesium chloride ($MgCl_2$) was shown to be detrimental to adenoviral stability. Therefore, in a preferred embodiment, the formulation according to this disclosure is free from magnesium chloride.

In a preferred embodiment, the virus formulation according to this disclosure comprises sodium chloride (NaCl). In a preferred embodiment, the concentration of sodium chloride is ranging between about 10 mM and 250 mM, e.g., between about 20 mM and 200 mM, e.g., between about 30 mM and 150 mM, e.g., between about 50 mM and 100 mM, e.g., about 80 mM.

The formulations of this disclosure comprise at least one non-ionic detergent (also named non-ionic surfactant) added to reduce adsorption to container surfaces as well as possibly providing increased virus stabilization (e.g., by reducing aggregation). Non-ionic detergents for use in the formulations of this disclosure include, but are not limited to, polyoxyethylene sorbitan fatty acid esters including, but not limited to, Polysorbate-80 (TWEEN® 80), Polysorbate-60 (TWEEN® 60), Polysorbate-40 (TWEEN® 40), and Polysorbate-20 (TWEEN® 20), and the PLURONIC® series of non-ionic surfactants (e.g., PLURONIC® 121).

In a preferred embodiment, the concentration of non-ionic detergent is ranging between about 0.001% (w/w) to 1% (w/w), e.g., between about 0.005% (w/w) to 0.5% (w/w), e.g., between about 0.01% (w/w) to 0.1% (w/w), e.g., between about 0.01% (w/w) to 0.05% (w/w), e.g., between about 0.015% (w/w) to 0.03% (w/w), e.g., about 0.025% (w/w).

In a preferred embodiment, the virus formulation according to this disclosure comprises Polysorbate-80. The concentration of Polysorbate-80 is preferably ranging between about 0.001% (w/w) to 1% (w/w), e.g., between about 0.005% (w/w) to 0.5% (w/w), e.g., between about 0.01% (w/w) to 0.1% (w/w), e.g., between about 0.01% (w/w) to 0.05% (w/w), e.g., between about 0.015% (w/w) to 0.03% (w/w), e.g., about 0.025% (w/w).

In a preferred embodiment, the virus formulation according to this disclosure further comprises EDTA. In a more preferred embodiment, the concentration of EDTA is ranging between about 0.05 mM to 0.2 mM, e.g., between about 0.05 mM to 0.15 mM, e.g., between about 0.08 mM to 0.12 mM, e.g., about 0.1 mM.

In another preferred embodiment, the virus formulation according to this disclosure further comprises ethanol. In a more preferred embodiment, the concentration of ethanol is ranging between about 0.1% (w/w) to 1% (w/w), e.g., between about 0.2% (w/w) to 0.8% (w/w), e.g., between about 0.2% (w/w) to 0.6% (w/w), e.g., about 0.4% (w/w).

In a preferred embodiment, when the virus formulation according to this disclosure comprises ethanol, it must not necessarily comprise EDTA at the same time.

In view of the discussion above, this disclosure relates to a formulation containing an adenovirus, such as a recombinant Ad5, Ad26 or Ad35, that can, e.g., be used in gene therapy and/or gene vaccination applications, which show improved stability properties as compared to the best performing formulation known in the art (disclosed in Evans et al. 2004) and which at least contains a citrate buffer, HBCD as a cryoprotectant, a salt, and a surfactant.

A particular embodiment of this disclosure relates to such a recombinant adenovirus formulation that is buffered with a citrate to a pH ranging between 5.5 and 6.5, and further comprises hydroxypropyl-beta-cyclodextrin (HBCD), a salt, a non-ionic detergent, and a 2- or 4-carbon alcohol.

In a preferred embodiment according to this disclosure, the formulation comprises a citrate buffer with a pH ranging from about pH 5.5 to pH 6.5, comprises HBCD as the cryoprotectant, NaCl as the salt, Polysorbate-80 as the surfactant and a 2- or 4-carbon alcohol as an additional unprecedented cryoprotectant.

In another preferred embodiment according to this disclosure, the formulation comprises a citrate buffer with a pH ranging from about pH 5.5 to pH 6.5, comprises HBCD as the cryoprotectant, NaCl as the salt, Polysorbate-80 as the surfactant and EDTA.

In another preferred embodiment according to this disclosure, the formulation comprises a citrate buffer with a pH ranging from about pH 5.5 to pH 6.5, comprises HBCD as the cryoprotectant, NaCl as the salt, Polysorbate-80 as the surfactant and ethanol as an additional unprecedented cryoprotectant.

In another preferred embodiment according to this disclosure, the formulation comprises a citrate buffer with a pH ranging from about pH 5.5 to pH 6.5, comprises HBCD as the cryoprotectant, NaCl as the salt, Polysorbate-80 as the surfactant. This formulation further comprises ethanol and is free of EDTA.

In a preferred embodiment according to this disclosure, the formulation has a pH ranging between about 5.9 and 6.2, and comprises citrate at a concentration ranging between about 10 and 25 mM; HBCD at a concentration ranging between 4% (w/w) and 6% (w/w); NaCl at a concentration ranging between 70 mM and 100 mM; Polysorbate-80 at a concentration ranging between about 0.018% (w/w) and 0.035% (w/w); and ethanol at a concentration ranging between about 0.3% (w/w) to 0.45% (w/w).

In another preferred embodiment according to this disclosure, the formulation has a pH ranging between about 5.8 and 6.2, and comprises citrate at a concentration ranging between about 15 and 25 mM; HBCD at a concentration ranging between 3% (w/w) and 8% (w/w); NaCl at a concentration ranging between 50 mM and 100 mM; Polysorbate-80 at a concentration ranging between about 0.01% (w/w) and 0.03% (w/w); and EDTA at a concentration ranging between about 0.05 mM to 0.15 mM.

In another preferred embodiment according to this disclosure, the formulation has a pH ranging between about 5.9 and 6.2, and comprises citrate at a concentration ranging between about 10 and 25 mM; HBCD at a concentration ranging between 4% (w/w) and 6% (w/w); NaCl at a concentration ranging between 70 mM and 100 mM; Polysorbate-80 at a concentration ranging between about 0.018% (w/w) and 0.035% (w/w); and EDTA at a concentration ranging between about 0.05 mM to 0.15 mM.

In an even more preferred embodiment of this disclosure, the formulation is buffered with about 20 mM citrate to a pH of about 6; HBCD is present at a concentration of about 5% (w/w); NaCl is present at a concentration of about 80 mM; the surfactant is Polysorbate-80 at a concentration of about 0.025% (w/w); and EDTA is present at a concentration of about 0.1 mM.

In an even more preferred embodiment of this disclosure, the formulation is buffered with about 20 mM citrate to a pH of about 6; HBCD is present at a concentration of about 5% (w/w); NaCl is present at a concentration of about 80 mM; the surfactant is Polysorbate-80 at a concentration of about 0.025% (w/w); and ethanol is present at a concentration of about 0.4% (w/w). Additionally, combinations of the above-mentioned factors can be used.

In one embodiment, the formulations according to this disclosure are contained in a vial such as, e.g., DIN 2R type I borosilicate glass vial. In another embodiment, the formulations are contained in a bag. Bags that contain the formulations of this disclosure may comprise layers made of, e.g., Ethylene Vinyl Acetate Copolymer (EVA) or Ethyl Vinyl Alcohol (EVOH). In yet another embodiment of this disclosure, the formulations are contained in a syringe.

The recombinant virus formulations described herein can be administered to the vertebrate host (preferably a mammalian host and especially a human recipient) by any means known in the art. These routes of delivery include, but are not limited to, intramuscular injection, intraperitoneal injection, intravenous injection, inhalation or intranasal delivery, oral delivery, sublingual administration, subcutaneous administration, transdermal administration, intradermal administration, intraductal salivary gland administration, transcutaneous administration or percutaneous administration. In a preferred embodiment, the formulation of this disclosure is compatible with parenteral administration.

In accordance with the formulations disclosed herein, this disclosure also relates to methods of preserving an adenovirus that comprise preparing virus-containing formulations as disclosed herein, such formulations that result in improved viral stability when stored below −65° C. and in about the 2° C. to 8° C. range and possibly higher, while also being compatible with parenteral administration, especially parenteral administration to humans.

Another aspect of this disclosure, therefore, relates to methods of preserving an adenovirus that comprise preparing a formulation as disclosed herein and storing the formulation at a temperature ranging between 2° C. and 8° C.

The following examples are provided to illustrate this disclosure without, however, limiting the same hereto.

EXAMPLES

Example 1

Experimental Design and Methodology

After having tested several different formulations, one formulation outperformed the others. This new formulation was named "Formulation B" and comprises 5% (w/w) HBCD, 20 mM citrate, 0.02% (w/w) PS-80 and 75 mM NaCl at a pH of 6.0.

Two Adenoviral (Ad35.TB-S and Ad26.Mosl.Gag-Pol) preparations (one comprising a serotype 35 adenovirus (Ad35) and one comprising a serotype 26 adenovirus (Ad26)) have been buffer-exchanged using PD-10 columns (GE Healthcare) into Formulation B.

Both adenoviral preparations have also been formulated in a "control formulation" that was described in Evans et al. 2004 and that was the best formulation available thus far. The "control formulation" comprises 10 mM Tris, 10 mM Histidine, 1 mM $MgCl_2$, 75 mM NaCl, 5% (w/w) sucrose, 0.02% (w/w) PS-80, 0.1 mM EDTA, 0.4% (w/w) EtOH, at a pH of 7.4.

Per formulation, 12 columns were used; eluates were pooled, sterile filtrated and stored at 2° C.-8° C. in a glass bottle. Samples were taken for viral titer determination by vp-QPCR and all titers were adjusted with the appropriate buffer formulation to $1.7 \times 10^{11}$ vp/mL. Subsequently, the formulations were filled into glass vials (0.7 mL per vial), stoppered and capped.

The t=0 samples (control, six vials per group) were stored directly at ≤−65° C. Subsequently, six vials per group (n=6) were incubated at 25° C. and frozen at ≤−65° C. at t=10, 20, 30, 40, 50, 60, 65, 70, 75, 80 and 90 days until sample analysis by QPA was performed in triplicate per sample.

In addition, t=0 samples for vectors in both formulations were analyzed by TMA (Thermal Melting Assay) to determine the capsid melting temperature. A higher melting temperature correlates to higher thermal stability of the viral capsid. End point samples (t=90 days) were also analyzed by Reverse Phase High Performance Liquid Chromatography (RP-HPLC) and Differential Centrifugal Sedimentation (DCS) and compared to t=0 controls.

Results and Conclusion

Figure 2:
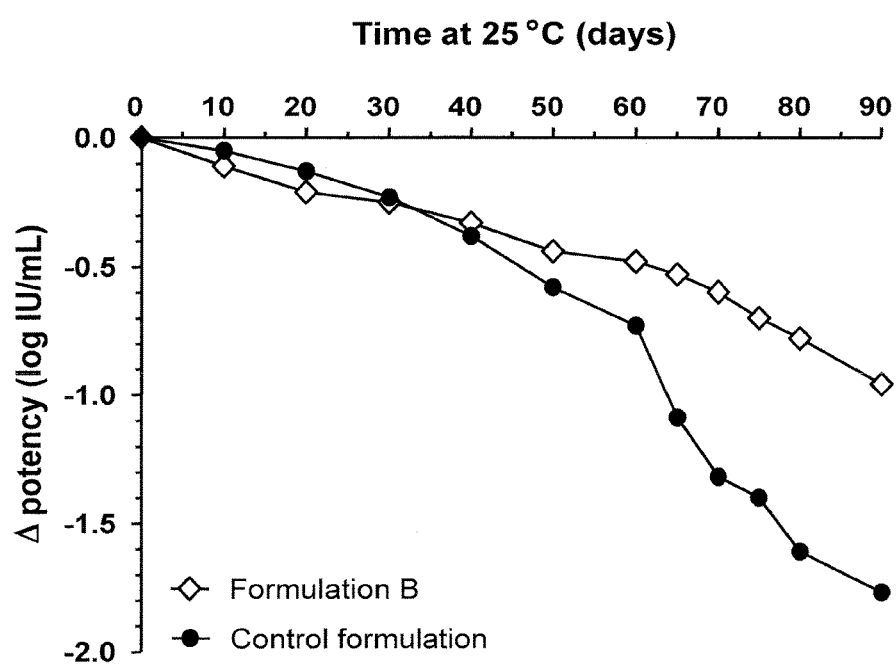
FIG. 2: Potency (in log IU/mL) loss (Δ) of Ad35 during accelerated temperature at 25° C. in Formulation B (open diamonds) and control formulation (closed circles). Mean Δ potency (n=4) is shown, reflecting potency$_{stressed\ sample}$−potency$_{control\ sample}$. Potency has been measured by QPA.

After the completion of the study, all samples were analyzed by QPA and the loss in potency was expressed as deltas by subtracting the t=0 values. The formulation B, according to this disclosure (open diamonds), significantly (p=1.44E-05) outperformed the control formulation (closed circles) leading to less degradation over time and a longer predicted shelf-life (Table 1) for both adenoviruses (FIGS. 1 and 2). With Statistical Analysis System (SAS software), linear (Ad26) and quadratic (Ad35) models were fitted on the potency data using time and the square of the time as fixed effects. While the fixed "time" effect represents the linear decrease in potency, the fixed "time*time" effect represents the curvature of this decrease. Both effects were used in the model to evaluate their significance. The Akaike Information Criterion (AIC) is a measure for the relative quality of the statistical model, taking into account the complexity of the model and its accuracy of fit. The smaller the AIC, the better the model fits. In the linear model, the slope represents the potency degradation rate. By comparing slopes, the best buffer (lowest slope) can be identified.

Shelf-lives correspond to the time points for which the lower limit of this interval pass under a given specification (i.e., decrease in potency). For the quadratic model, to compute shelf-life, the two-sided 95% confidence intervals around the mean were taken. Keeping only the lower bound for the shelf-life assessment leads to a 97.5% confidence level for the univariate lower confidence interval. The intercepts (reflecting potency at t=0) were averaged and removed from the raw data and the model. The shelf-lives were computed for both formulations.

TABLE 1

Shelf-lives at 25° C. derived from statistical analysis of degradation curves (FIGS. 1 and 2).

| | Formulation B vs Control |
|---|---|
| Ad26-shelf-life | 36.1% longer |
| Ad35-shelf-life | 50.0% longer |

Figure 3:
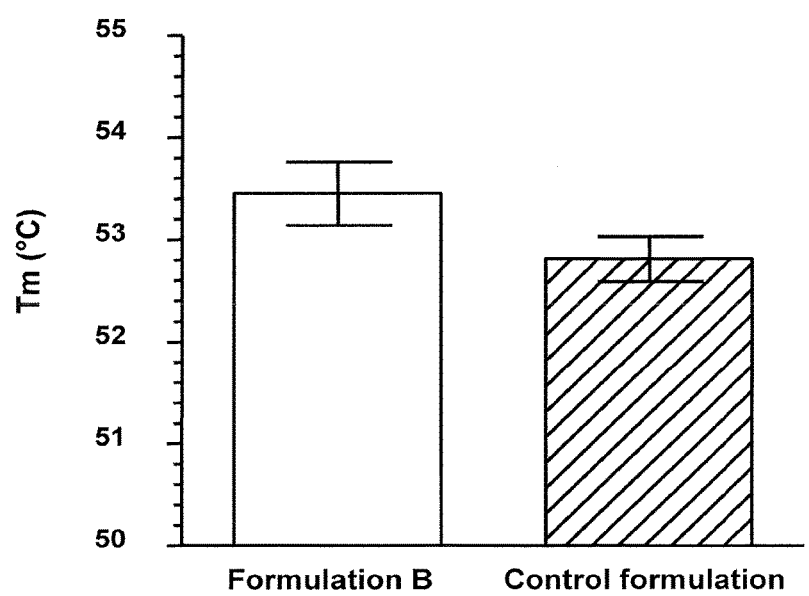
FIG. 3: Thermal melting point of Ad26 in Formulation B and control formulation. TMA (Thermal melting assay) analysis (n=3) for Ad26 was performed on t=0 samples.
Figure 4:
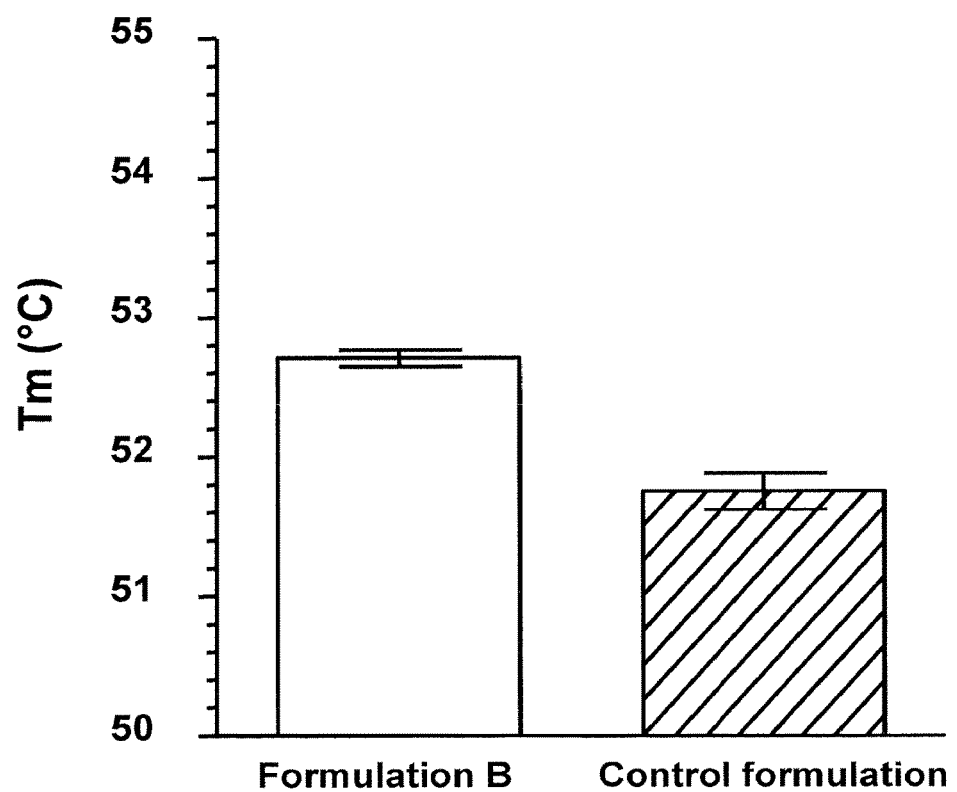
FIG. 4: Thermal melting point of Ad35 in Formulation B and control formulation. TMA (Thermal melting assay) analysis (n=3) for Ad35 was performed on t=0 samples.

The RP-HPLC did not show any signs of Adeno protein modifications nor oxidation. The DCS did not reveal any signs of aggregation. Furthermore, the formulation according to this disclosure led to a significantly increased melting temperature for both Ad26 (FIG. 3) and Ad35 (FIG. 4) compared to the control formulation, indicating the increased stability of the adenoviruses in formulation B.

Example 2

Experimental Design and Methodology

After the experiments described in Example 1, formulation B was modified by adding or omitting one or several components (NaCl, Ethanol, EDTA, or combinations thereof) yielding eight experimental formulations (A to H, see Table 2) that were compared to the control formulation (described in Evans et al. and specified hereinabove). All formulations contain 5% HBCD, 20 mM citrate and 0.02% PS-80. As indicated in Table 2, the formulations further comprise 75 mM NaCl, 0.1 mM EDTA and/or 0.5% ethanol (EtOH). Adenoviruses (Ad26) were incubated in these nine formulations for 69 days at 25° C. or 16 days at 35° C. or exposed to 30 cycles of freeze/thawing followed by agitation (1 day at room temperature). Potency loss was assessed by QPA and expressed as delta (t=0 subtracted) Ct (threshold cycle) values. Additionally, the absorbance at 350 nm was read as a measure for turbidity and the intrinsic fluorescence was measured to detect conformational protein changes and aggregation. Finally, a TMA and vp-QPCR were performed to determine the melting temperature and the vp/IU ratio.

TABLE 2

Formulation composition. All formulations contain 5% HBCD, 20 mM citrate and 0.02% PS-80, some supplemented with NaCl: 75 mM, EDTA: 0.1 mM and/or ethanol (EtOH): 0.5% (w/w).

| Formulation | NaCl | EDTA | EtOH |
|---|---|---|---|
| A | − | − | − |
| B | + | − | − |
| C | − | + | − |
| D | + | + | − |
| E | − | − | + |
| F | + | − | + |
| G | − | + | + |
| H | + | + | + |

Results and Conclusion

Figure 5:
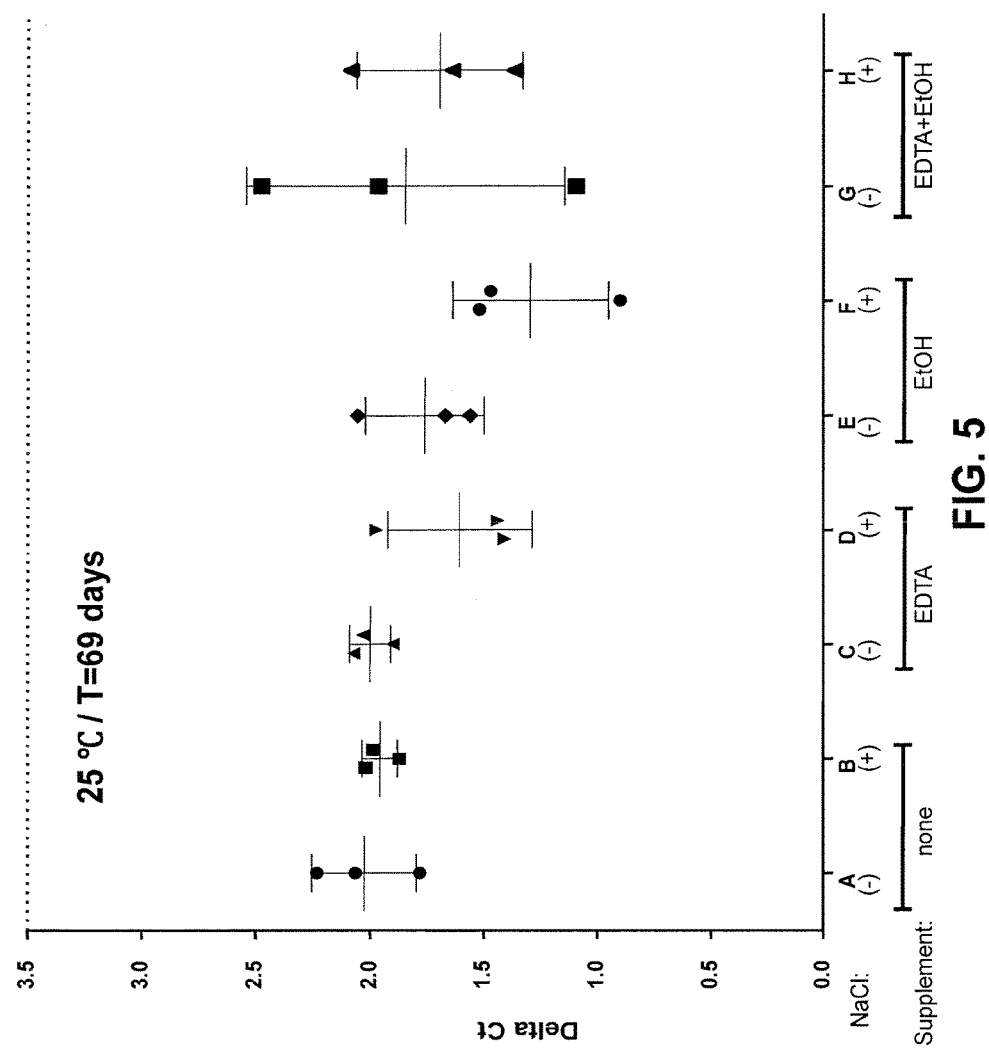
FIG. 5: Delta Ct (ΔCt) values of Ad26 in Formulation B with and without NaCl, EDTA, ethanol and combinations thereof after 69 days at 25° C. The ΔCt values directly correlate with a loss in potency, where a higher number means more potency loss.

Based on the 25° C. stability results shown in FIG. 5, it can be concluded that the addition of NaCl in combination with EDTA (C and D) or ethanol (E and F) is clearly beneficial for the viral stability, where ethanol clearly outperforms EDTA. Unexpectedly, the combination of both EDTA and ethanol with or without NaCl does not lead to a more stable formulation (G and H). This is contrary to what would have been expected from the prior art, e.g., Altaras et al., 2005, and Evans et al., 2004, wherein the specific combination of EDTA/EtOH is commonly referred as being an inhibitor of free-radical oxidation and therewith a great enhancer of adenoviral stability.

Figure 6:
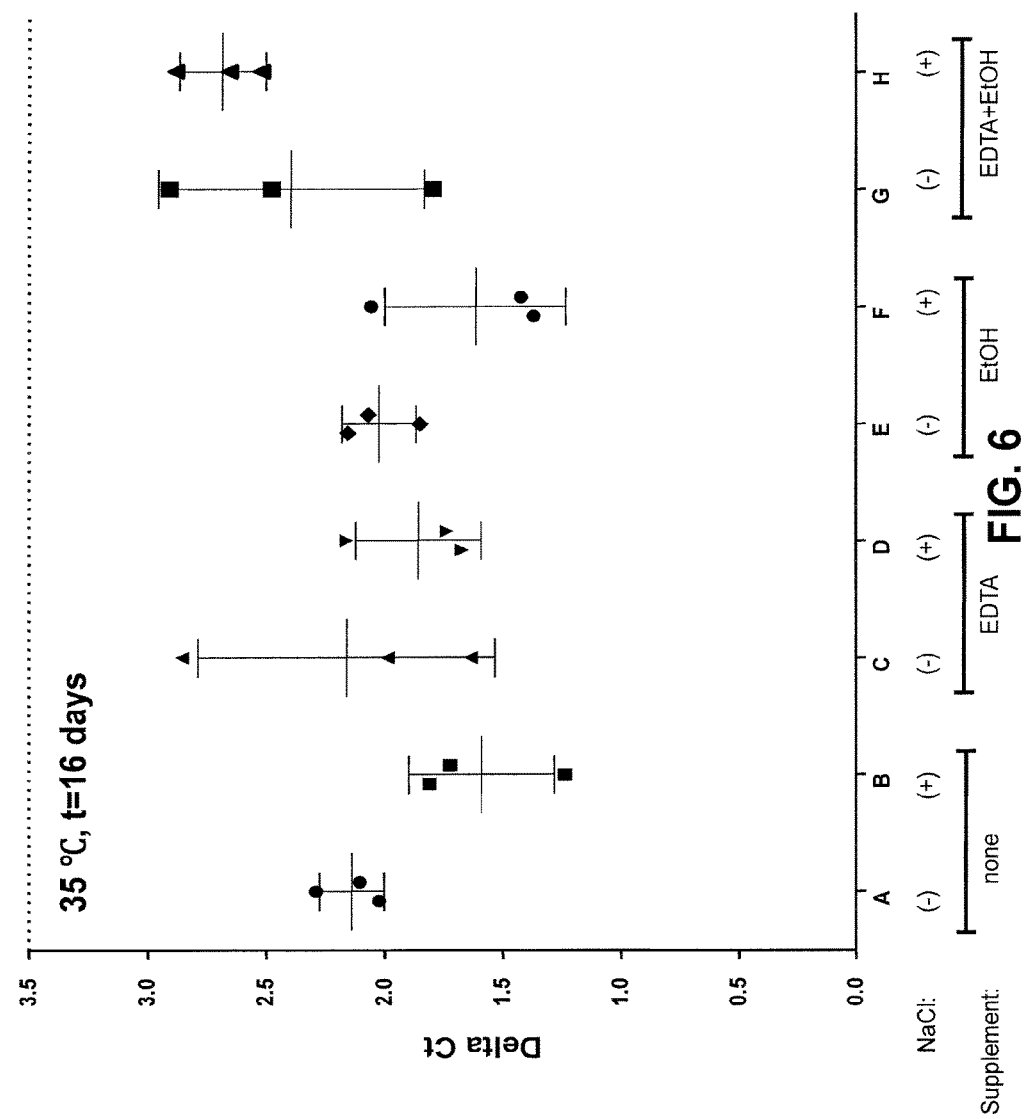
FIG. 6: Delta Ct (ΔCt) values of Ad26 in Formulation B with and without NaCl, EDTA, ethanol and combinations thereof after 16 days at 35° C. The ΔCt values directly correlate with a loss in potency, where a higher number means more potency loss.

Moving to a harsher model, 35° C. for 16 days, the discriminating power becomes more pronounced, as can be seen in FIG. 6. Clearly, the addition of NaCl is improving the stability and the beneficial effect of ethanol is confirmed in FIG. 6. Surprisingly, the combination of EDTA together with ethanol, with or without NaCl, has a clear negative effect on the viral stability. This goes against the common perception that the combination of EDTA/EtOH performs well as an inhibitor of free-radical oxidation (e.g., Altaras et al., 2005, and Evans et al., 2004). Taken together, both thermal stressors show the beneficial effect of NaCl in combination with either EDTA or ethanol in this particular formulation.

Figure 7:
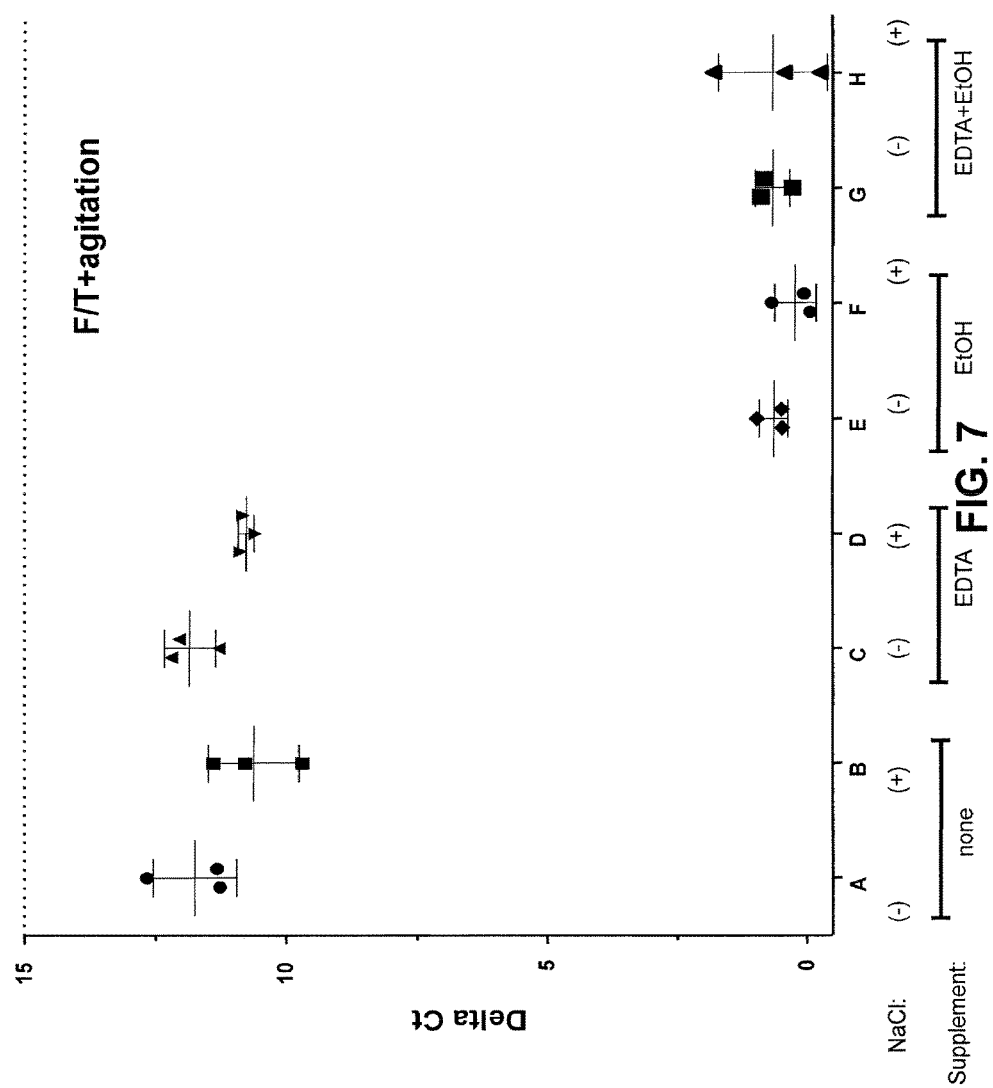
FIG. 7: Delta Ct (ΔCt) values of Ad26 in Formulation B with and without NaCl, EDTA, ethanol and combinations thereof after 30 cycles of freeze/thawing followed by 1 day of agitation. The ΔCt values directly correlate with a loss in potency, where a higher number means more potency loss.

To investigate the performance of the formulations with a different degradation route, the formulations (A to H) were exposed to a freeze/thaw cycle and agitation stress (FIG. 7).

The observed effects are both pronounced and unexpected. Clearly, EDTA (C and D) did not have any effect. On the other hand, ethanol strongly protected against freeze/thaw damage and consequently worked as a cryoprotectant (E to H).

Figure 8:
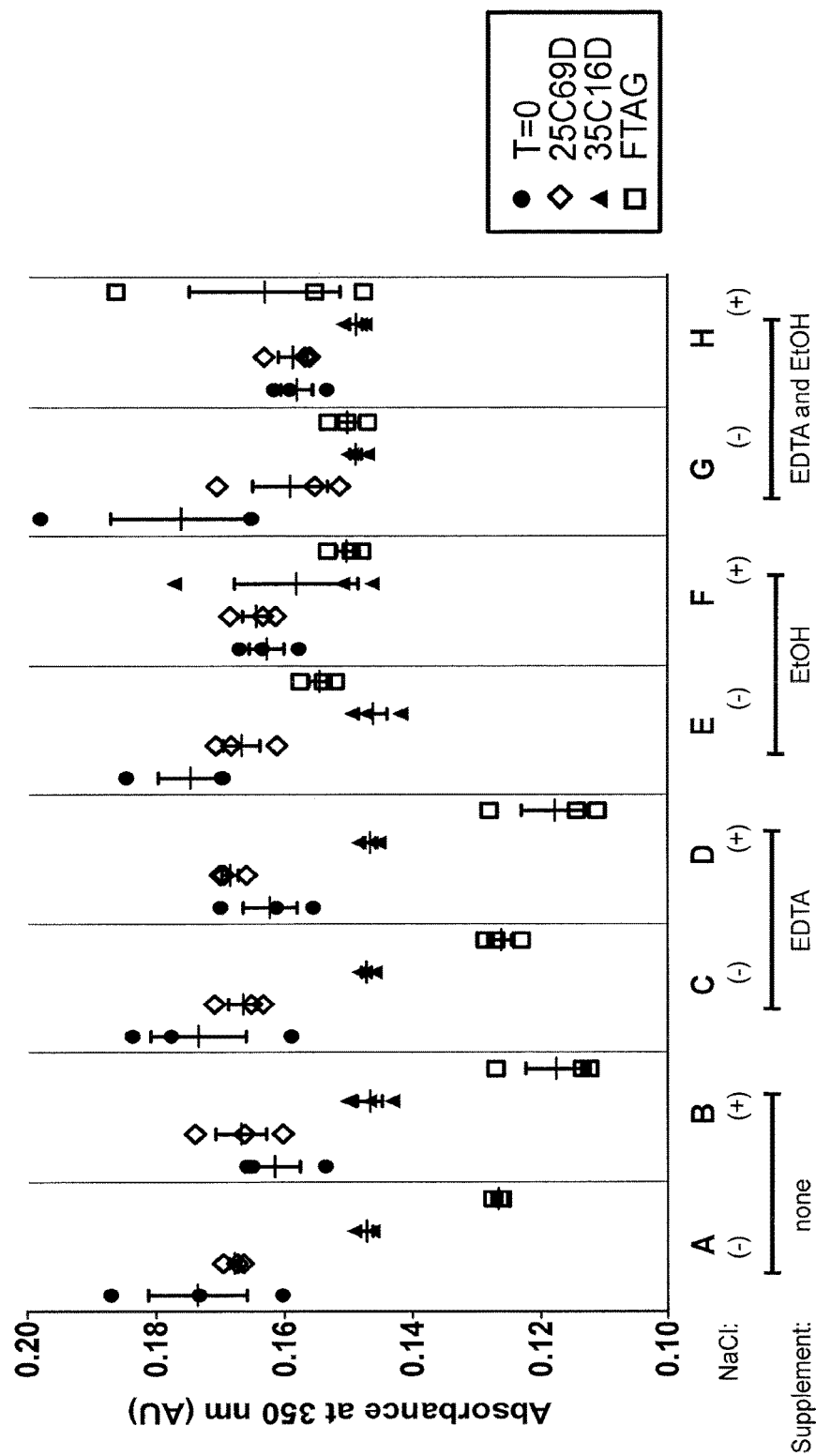
FIG. 8: Turbidimetry measured by absorbance at 350 nm of Ad26 in Formulation B with and without NaCl, EDTA, ethanol and combinations thereof of t=0 (closed circles), 25° C. for 69 days (open diamonds), 35° C. for 16 days (closed triangles) and 30 cycles of freeze/thawing followed by agitation (open rectangles).

These unpredictable results have been confirmed by absorbance readings at 350 nm in a turbidimetry assay (FIG. 8). Freeze/thawing (empty squares in FIG. 8) led to a decrease in turbidity compared to t=0, in the formulations without ethanol. This decrease was most likely due to disintegration of viral particles. In line with these observations, accelerated temperature stress (black triangles in FIG. 8) also resulted in a decrease in turbidity in the ethanol-free formulations, whereas the formulation with ethanol, specifically formulation F, displays no significant change compared to the t=0 (black circles in FIG. 8) samples.

Figure 9:
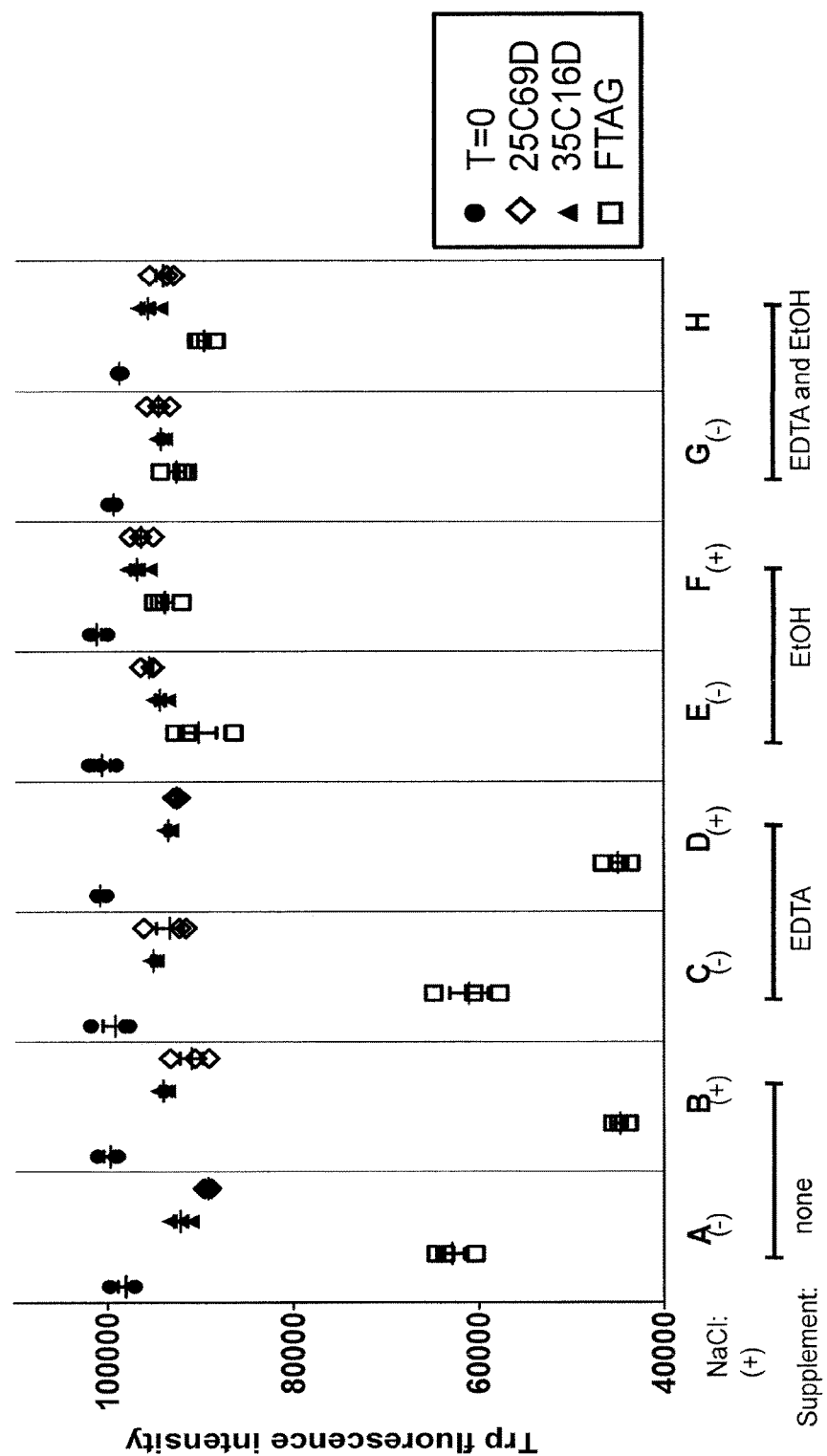
FIG. 9: Intrinsic fluorescence of Ad26 in Formulation B with and without NaCl, EDTA, ethanol and combinations thereof of t=0 (closed circles), 25° C. for 69 days (open diamonds), 35° C. for 16 days (closed triangles) and 30 cycles of freeze/thawing followed by agitation (open rectangles).

In addition, the intrinsic fluorescence (FIG. 9) further confirms the previous observations. The formulation without ethanol led to a substantial decrease in tryptophan fluorescence after freeze/thaw stress compared to t=0 (empty squares in FIG. 9), indicating severe conformational changes in the viral capsid. In sharp contrast, the formulations with ethanol are protecting the virus from this stressor. Thermal stress had only a minor impact on the formulations containing ethanol.

Figure 10:
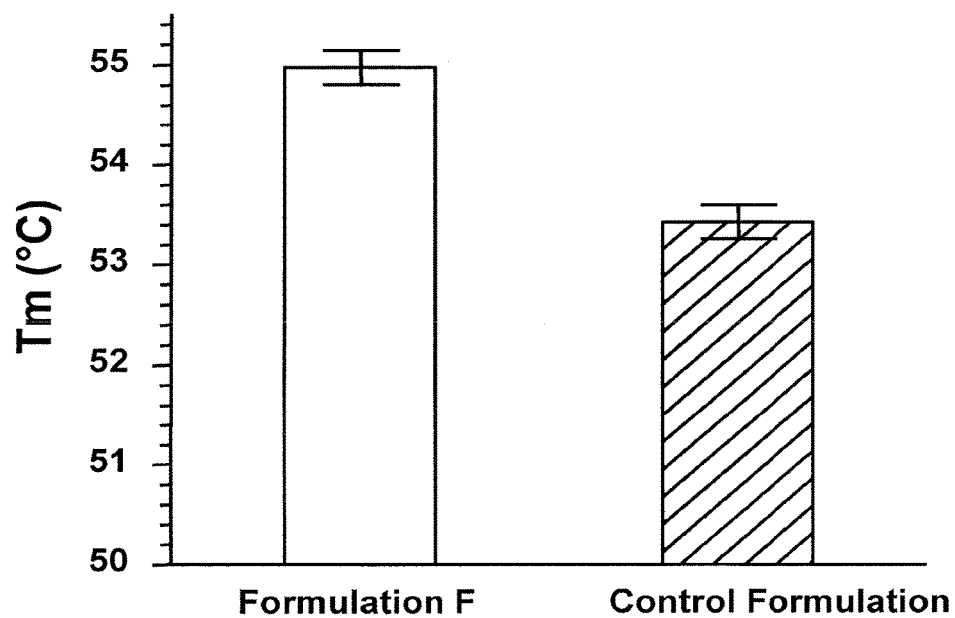
FIG. 10: Thermal melting point of Ad26 in Formulation F and control formulation. TMA analysis (n=3) for Ad26 was performed on t=0 samples.

TMA data revealed a significantly increased melting temperature of formulation F compared to the control formulation (FIG. 10), which is indicative of a more stable viral capsid in formulation F.

Importantly, the vp/IU ratio, reflecting the infectious proportion of the viral preparation (indicative of the quality of the virus particles), revealed higher values (less infectious particles per total amount of particles) in the control formulation compared to Formulation F after exposure to accelerated temperature (25° C.), see Table 3. This shows that formulation F is able to preserve the infectivity of adenoviruses in a much greater way compared to the control formulation.

TABLE 3 vp/IU ratios for Formulation F and control formulation at t = 0 and t = 61 at 25° C.

|  | Unstressed | Stressed |
| --- | --- | --- |
| Control Formulation | 39 | 93 |
| Formulation F | 32 | 61 |

Example 3

Experimental Design and Methodology

To define the formulation buffer design space, the robustness range for each excipient was evaluated. After having selected the factors, an experimental range was defined for each component as reported in Table 4.

Design of experiment (DOE) approach was followed to map the experimental space. Using a design with a low and a high level for each of six factors (Table 4), 15 formulations were prepared—including three central points—to study the effect of each factor and possible interactions between the factors (Table 5) with high statistical power.

TABLE 4

Factors and levels used to compile the experimental space for the study

| Formulation factor | Buffer F | Target level Form. buffer F | Low level | High level |
| --- | --- | --- | --- | --- |
| Buffer composition | pH | 6.0 | 5.8 | 6.2 |
|  | Citrate (mM) | 20 | 10 | 25 |
|  | HBCD (w/w) | 5 | 3 | 6 |
|  | EtOH (w/w) | 0.4 | 0.3 | 0.5 |
|  | PS-80 (w/w) | 0.02 | 0.015 | 0.04 |
|  | NaCl (mM) | 75 | 50 | 100 |

TABLE 5

Design of experiment. Fifteen formulations were independently prepared, including three central points (gray rows), following the factors and levels used to compile the experimental space for the study.

| Name | pH | Citrate | HBCD | EtOH | PS-80 | NaCL | Comments |
| --- | --- | --- | --- | --- | --- | --- | --- |
| F-01 | 6.2 | 20 | 3 | 0.5 | 0.04 | 50 |  |
| F-02 | 5.8 | 25 | 3 | 0.3 | 0.04 | 75 |  |
| F-00.1 | 6 | 20 | 5 | 0.4 | 0.02 | 75 | central point |
| F-03 | 6 | 10 | 3 | 0.3 | 0.015 | 50 |  |
| F-00.2 | 6 | 20 | 5 | 0.4 | 0.02 | 75 | central point |
| F-04 | 6 | 25 | 6 | 0.5 | 0.04 | 100 |  |
| F-00.3 | 6 | 20 | 5 | 0.4 | 0.02 | 75 | central point |
| F-05 | 6.2 | 25 | 6 | 0.3 | 0.02 | 50 |  |
| F-06 | 5.8 | 10 | 6 | 0.4 | 0.04 | 50 |  |
| F-07 | 6.2 | 10 | 6 | 0.5 | 0.015 | 75 |  |
| F-08 | 5.8 | 10 | 3 | 0.5 | 0.02 | 100 |  |
| F-09 | 6.2 | 25 | 3 | 0.4 | 0.015 | 100 |  |
| F-10 | 5.8 | 20 | 6 | 0.3 | 0.015 | 100 |  |
| F-11 | 5.8 | 25 | 5 | 0.5 | 0.015 | 50 |  |
| F-13 | 6.2 | 10 | 5 | 0.3 | 0.04 | 100 |  |

To assess appropriate levels for each excipient and pH (the formulation robustness), each group was filled in glass vials and subjected to ten freeze/thaw (F/T) cycles, followed by 1 day agitation at 200 rpm at room temperature (RT) and storage for 7 days at 35° C. (accelerated degradation model). Potency by QPA (n=3) was then used as read out.

An Ad26 preparation has been buffer-exchanged using PD-10 columns (GE Healthcare) into each of the formulations listed in Table 5. Eluates of each formulation were pooled, sterile filtrated and stored at 2° C.-8° C. in a glass bottle. Samples were taken for viral titer determination by vp-QPCR and all titers were adjusted with the appropriate formulation to $1\times10^{11}$ vp/mL. Subsequently, the formulations were filled into glass vials (0.75 mL per vial), stoppered and capped. The t=0 samples (control, six vials per group) were stored directly at ≤−65° C. Subsequently, four vials per group (n=4) were incubated, freeze/thawed, agitated and stored at 35° C. for 7 days (Table 6) until sample analysis by QPA was performed in triplicate per sample.

Results and Conclusion

After the completion of the study, all samples were analyzed by QPA and the loss in potency was expressed as deltas by subtracting the t=0 values. This data was used for the statistical analysis.

The output of the statistical analysis was the probability of success, in which success is defined as a stable formulation, meeting the specifications set for the selected critical quality attribute (CQA): potency. Equivalence testing was carried out between T0 and after stress. To compare equivalence, acceptance criteria were defined on the maximum loss of potency (IU/mL) that can be tolerated. In this experiment, the tolerated potency loss was defined as ΔPotency limit ≥−0.30 log IU/mL.

The experimental data obtained are shown in Table 6 and were used to reduce the experimental domain and compute a Design Space, based on potency.

The data contains 45 observations. There are 12 different buffers that have been tested in triplicate and an additional one that has been prepared three times separately and each independent preparation has been tested in triplicate (central points).

TABLE 6

Experimental values for each formulation expressed as ΔPotency (log_IU/mL)

| Group Name | ΔPotency (log_IU per mL) | Remarks |
|---|---|---|
| F-01 | −0.35 | |
| F-01 | −0.29 | |
| F-01 | −0.33 | |
| F-02 | −0.29 | |
| F-02 | −0.29 | |
| F-02 | −0.32 | |
| F-00.1 | −0.28 | CENTRAL POINT |
| F-00.1 | −0.27 | CENTRAL POINT |
| F-00.1 | −0.26 | CENTRAL POINT |
| F-03 | −0.3 | |
| F-03 | −0.33 | |
| F-03 | −0.24 | |
| F-00.2 | −0.2 | CENTRAL POINT |
| F-00.2 | −0.28 | CENTRAL POINT |
| F-00.2 | −0.22 | CENTRAL POINT |
| F-04 | −0.18 | |
| F-04 | −0.26 | |
| F-04 | −0.24 | |
| F-00.3 | −0.21 | CENTRAL POINT |
| F-00.3 | −0.18 | CENTRAL POINT |
| F-00.3 | −0.16 | CENTRAL POINT |
| F-05 | −0.2 | |
| F-05 | −0.18 | |
| F-05 | −0.2 | |
| F-06 | −0.33 | |
| F-06 | −0.25 | |
| F-06 | −0.25 | |
| F-07 | −0.18 | |
| F-07 | −0.27 | |
| F-07 | −0.14 | |
| F-08 | −0.31 | |
| F-08 | −0.28 | |
| F-08 | −0.25 | |
| F-09 | −0.28 | |
| F-09 | −0.26 | |
| F-09 | −0.2 | |
| F-10 | −0.27 | |
| F-10 | −0.26 | |
| F-10 | −0.26 | |
| F-11 | −0.31 | |
| F-11 | −0.27 | |
| F-11 | −0.25 | |
| F-13 | −0.22 | |
| F-13 | −0.15 | |
| F-13 | −0.18 | |

The following model has been fitted to the data:
delta_log_potency[i]~normal(mu[i], sigma);
for(i in 1:Nobs){
mu[i]<−alpha_0+
  alpha_pH*pH[i]+
  alpha_Citrate*Citrate[i]+
  alpha_HBCD*HBCD[i]+
  alpha_EtOH*EtOH[i]+
  alpha_PS_80*PS_80[i]+
  alpha_NaCl*NaCl[i]+
  alpha_HBCD2*HBCD[i]*HBCD[i]+
  alpha_PS_802*PS_80[i]*PS_80[i]+
  alpha_pH_HBCD*pH[i]*HBCD[i]+
  alpha_pH_NaCl*pH[i]*NaCl[i]+
  alpha_r_Batch[batch[i]];

where alpha-r-batch represents the random batch and sigma the residual error.

To obtain predictions from the model to obtain a risk-based Design Space approach, the Bayesian framework has been adopted because the predictive joint distribution of the CQA given the formulation parameters can be derived easily (see Peterson et al. and Lebrun et al.). The risk-based Design Space is defined using the following probability statement:

$$\text{Design Space} = \{\tilde{x} \in \chi | P(CQAs \in \Lambda | X = \tilde{x}, data) \geq \pi\} \quad (1)$$

In other words, the Design Space is a region of the experimental domain $\chi$ (often called knowledge space) where the posterior probability that the CQAs are within specifications ($\Lambda$), is higher than a specified quality level $\pi$, given the observed data. This notation makes implicit the inclusion of the uncertainty included in the statistical model. The probability is a direct measure of the guarantees to meet specifications jointly. To compute this probability, the statistical models can be written as the following generic linear equation. For the $j^{th}$ CQA, a model is adjusted:

$$y_i = Xb_j + e_i, \text{ with } e_i \sim N(0, \sigma_i^2) \quad (2)$$

where $y_i$ is any transformation applied to the ith CQA in order to obtain good statistical properties (e.g., identity, log or logit transformations), i=1, ..., 7. The model parameters $b_j$ and $\sigma_i^2$ are to be estimated (see articles above).

The posterior probability of Equation (1) is computed from the predictive distribution of new responses, identified as the following Student's distribution (indices i are dropped for simplicity):

$$\tilde{y} | \tilde{x}, \text{data} \sim t_{n-p}(\tilde{x}\hat{\beta}, S). \quad (3)$$

This three-parameter Student's distribution has n−p degrees of freedom (for n observations and p model parameters), is centered on the mean regression line $\tilde{x}\hat{\beta}$, computed from the ordinary least-square estimate of $\beta$: $\hat{\beta} = (X'X)^{-1}X'y$. $S = a.(1 + \tilde{x}'(X'X)^{-1}\tilde{x})$, where the parameter a is the residual sum of square, that is, $a = (y - X\hat{\beta})'(y - X\hat{\beta})$ Thus, S defines the scale of the Student's distribution. Variance estimator is computed as $S/(n-p)$.

To explore the experimental domain, it is not recommended to create a grid on five factors (because of a dimensionality problem: if two levels per factor were assessed, it would result in a 25-sized grid; if ten levels per factor, it would lead to a 105-sized grid, etc.). Instead, a number of random samples were created and explored as follows:
  a) Chose a high number random (uniformly distributed over $\chi$) operating conditions (factor settings) $\hat{x}_i$ within the experimental domain
  b) For each operating condition: carry out a high number of simulations:
Draw n* samples $\tilde{y}_{lj}|\tilde{x}_j$, data (l=1, ..., n*) from the predictive distributions as in Equation (3), for each CQA
  c) From the different simulations of CQA prediction, compute the proportion of samples within specifications.

Figure 11:
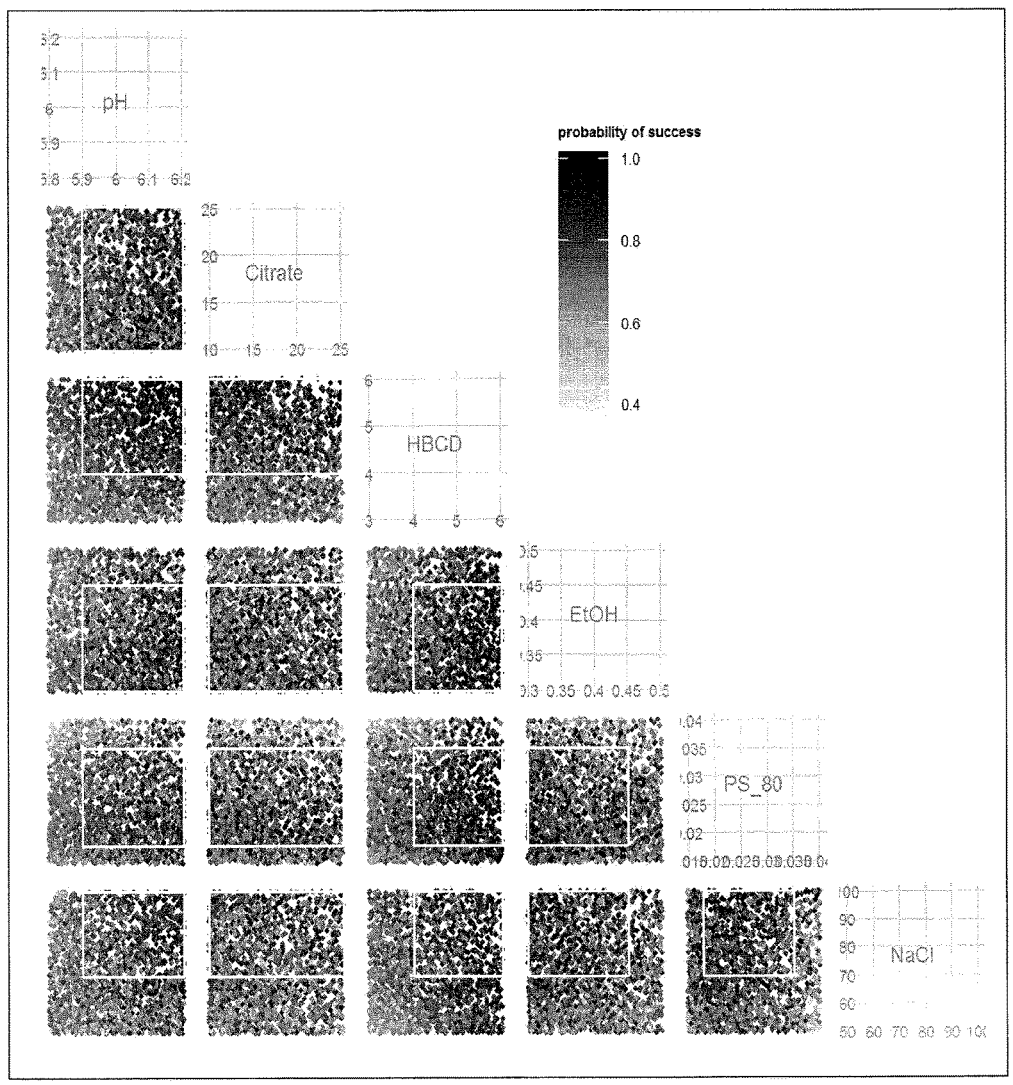
FIG. 11: Pair plot for the probability of success for CQA potency (Δ Potency limit ≥−0.30 log IU/mL) with stress condition freeze/thaw (FT)+agitation (AG)+storage at 35° C. The scale for the probability of success is from 0.4 (light grey) to 1 (black). The full experimental domain is explored. In the white square is the design space proposed based on the plot.

This proportion is the posterior probability estimate to obtain quality outputs given the Critical Quality Attributes and their specifications. Finally, it is proposed to visually assess the random operating distribution on pair plots of the projection of the results in two-dimensional spaces, to identify a Design Space (FIG. 11).

The computations were then adapted and factor ranges were reduced to maximize the probability of success for CQA potency in these ranges (Table 7), which reflect the so-called Normal Operating Ranges (NOR) and the Design Space. The ranges shown in Table 7 ensure the highest probability of success to have a stable formulation. These ranges thus ensure optimal product stability.

TABLE 7

Design Space with selected factor ranges (NOR)

| Formulation factor | Specification |
| --- | --- |
| pH | 5.9-6.2 |
| Citrate (mM) | 10-25 |
| HBCD (w/w) | 4-6 |
| EtOH (w/w) | 0.3-0.45 |
| PS-80 (w/w) | 0.018-0.035 |
| NaCl (mM) | 70-100 |

REFERENCES

Altaras N. E. et al. "Production and formulation of adenovirus vectors," *Advances in Biochemical Engineering*, Springer, Berlin, D E, vol. 99, 1 Nov. 2005.

Box G. E., W. G. Hunter, and J. S. Hunter. *Statistics for Experimenters: Design, Innovation, and Discovery* 2nd Edition, Wiley, 2005.

Bustin et al. 2009, "The MIQE Guidelines," *Clinical Chemistry* 55:4.

Evans R. K., D. K. Nawrocki, L. A. Isopi, D. M. Williams, D. R. Casimiro, S. Chin, M. Chen, D. M. Zhu, J. W. Shiver, and D. B. Volkin. "Development of stable liquid formulations for adenovirus-based vaccines," *J. Pharm. Sci.* 2004 October; 93(10):2458-75.

Lebrun et al., *Journal of Biopharmaceutical Statistics* 23:1330-1351, 2013.

Peterson J. J., *Journal of Biopharmaceutical Statistics* 18:959-975, 2008.

Radosevic K., A. Rodriguez, A. A. Lemckert, M. van der Meer, G. Gillissen, C. Warnar, R. von Eyben, M. G. Pau, and J. Goudsmit. The Th1 immune response to *Plasmodium falciparum* circumsporozoite protein is boosted by adenovirus vectors 35 and 26 with a homologous insert. *Clin Vaccine Immunol.* 2010 November; 17(11):1687-94.

Renteria S. S. et al. "Development of a nasal adenovirus-based vaccine: Effect of concentration and formulation on adenovirus stability and infectious titer during actuation from two delivery devices." *Vaccine*, vol. 28, no. 9, 25 Feb. 2010.

What is claimed is:

1. A method of preserving a recombinant adenovirus, the method comprising:
   a. preparing a recombinant adenovirus formulation, wherein the formulation comprises:
      i. a recombinant adenovirus;
      ii. a citrate buffer having a concentration of between about 5 mM and about 30 mM;
      iii. hydroxypropyl-beta-cyclodextrin (HBCD);
      iv. a salt; and
      v. a non-ionic detergent;
         wherein said formulation has a pH of between about 5.5 and about 6.5, and wherein the formulation is a liquid formulation, and
   b. storing said formulation at or below −65° C., wherein storing the formulation at or below −65° C. preserves the recombinant adenovirus.

2. The method of claim 1, wherein the concentration of the HBCD is between about 1% (weight/weight (w/w)) and about 10% (w/w).

3. The method of claim 1, wherein the salt is sodium chloride (NaCl), and the concentration of the NaCl is between about 20 mM and about 200 mM.

4. The method of claim 1, wherein the recombinant adenovirus formulation is free from magnesium chloride.

5. The method of claim 1, wherein the non-ionic detergent is Polysorbate-80, and the concentration of the Polysorbate-80 is between about 0.005% (w/w) and about 0.5% (w/w).

6. The method of claim 1, wherein the recombinant adenovirus formulation further comprises a 2-carbon or 4-carbon alcohol.

7. The method of claim 6, wherein the 2-carbon or 4-carbon alcohol is ethanol.

8. The method of claim 7, wherein the concentration of ethanol is between about 0.1% (w/w) and about 1% (w/w).

9. The method of claim 1, wherein the recombinant adenovirus is selected from a recombinant Ad26 or a recombinant Ad35.

10. The method of claim 1, wherein the concentration of the recombinant adenovirus is between about $1 \times 10^7$ vp/mL and about $1 \times 10^{13}$ vp/mL.

11. A method of preserving a recombinant adenovirus, the method comprising:
   a. preparing a recombinant adenovirus formulation, wherein the formulation comprises:
      i. a recombinant adenovirus;
      ii. a citrate buffer having a concentration of between about 5 mM and about 30 mM;
      iii. hydroxypropyl-beta-cyclodextrin (HBCD);
      iv. a salt; and
      v. a non-ionic detergent;
         wherein said formulation has a pH of between about 5.5 and about 6.5, and
         wherein the formulation is a liquid formulation, and
   b. storing said formulation at between about 2° C. and about 8° C., wherein storing the formulation at between about 2° C. and about 8° C. preserves the recombinant adenovirus.

12. The method of claim 11, wherein the concentration of the HBCD is between about 1% (weight/weight (w/w)) and about 10% (w/w).

13. The method of claim 11, wherein the salt is sodium chloride (NaCl), and the concentration of the NaCl is between about 20 mM and about 200 mM.

14. The method of claim 11, wherein the recombinant adenovirus formulation is free from magnesium chloride.

15. The method of claim 11, wherein the non-ionic detergent is Polysorbate-80, and the concentration of the Polysorbate-80 is between about 0.005% (w/w) and about 0.5% (w/w).

16. The method of claim 11, wherein the recombinant adenovirus formulation further comprises a 2-carbon or 4-carbon alcohol.

17. The method of claim 16, wherein the 2-carbon or 4-carbon alcohol is ethanol.

18. The method of claim 17, wherein the concentration of ethanol is between about 0.1% (w/w) and about 1% (w/w).

19. The method of claim 11, wherein the recombinant adenovirus is selected from a recombinant Ad26 or a recombinant Ad35.

20. The method of claim 11, wherein the concentration of the recombinant adenovirus is between about $1 \times 10^7$ vp/mL and about $1 \times 10^{13}$ vp/mL.

* * * * *